United States Patent
Bogyo et al.

(10) Patent No.: US 9,180,209 B2
(45) Date of Patent: Nov. 10, 2015

(54) NON-PEPTIDIC QUENCHED FLUORESCENT IMAGING PROBES

(75) Inventors: Matthew S. Bogyo, Redwood City, CA (US); Laura E. Edgington, Melbourne (AU); Martijn Verdoes, Nijmegen (NL)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 19 days.

(21) Appl. No.: 14/001,858

(22) PCT Filed: Feb. 24, 2012

(86) PCT No.: PCT/US2012/026601
§ 371 (c)(1),
(2), (4) Date: Feb. 3, 2014

(87) PCT Pub. No.: WO2012/118715
PCT Pub. Date: Sep. 7, 2012

(65) Prior Publication Data
US 2014/0140930 A1    May 22, 2014

Related U.S. Application Data

(60) Provisional application No. 61/447,526, filed on Feb. 28, 2011.

(51) Int. Cl.
C07D 249/12    (2006.01)
A61K 49/00     (2006.01)
C07D 249/04    (2006.01)
C07D 409/12    (2006.01)
C07D 409/14    (2006.01)
C07F 5/02      (2006.01)

(52) U.S. Cl.
CPC ......... *A61K 49/0052* (2013.01); *A61K 49/0021* (2013.01); *A61K 49/0032* (2013.01); *C07D 249/04* (2013.01); *C07D 409/12* (2013.01); *C07D 409/14* (2013.01); *C07F 5/022* (2013.01)

(58) Field of Classification Search
CPC ... A61K 49/0052; A61K 49/04; A61K 51/04; C07D 249/04; C07D 249/10; C07D 249/12
USPC .......................................................... 424/9.6
See application file for complete search history.

(56) References Cited

U.S. PATENT DOCUMENTS

| | | | |
|---|---|---|---|
| 5,989,823 A | 11/1999 | Jayasena et al. | |
| 6,399,392 B1 | 6/2002 | Haugland et al. | |
| 6,777,403 B2 | 8/2004 | Cheronis | |
| 6,906,037 B2 | 6/2005 | Little, II et al. | |
| 2002/0150961 A1 | 10/2002 | Bogyo et al. | |
| 2003/0228609 A1 | 12/2003 | Whateley | |
| 2004/0241679 A1 | 12/2004 | Lee | |
| 2005/0014160 A1 | 1/2005 | Kumaraswamy et al. | |
| 2006/0275843 A1 | 12/2006 | Nepveu et al. | |
| 2007/0036725 A1 | 2/2007 | Bogyo et al. | |
| 2009/0123372 A1* | 5/2009 | Kolb et al. | 424/1.89 |
| 2009/0252677 A1 | 10/2009 | Bogyo et al. | |
| 2009/0263830 A1 | 10/2009 | Packard et al. | |
| 2010/0068150 A1 | 3/2010 | Bogyo et al. | |
| 2012/0251459 A1 | 10/2012 | Lee et al. | |

FOREIGN PATENT DOCUMENTS

WO    01/86001 A1    11/2001

OTHER PUBLICATIONS

Lee et al., "Development of near-infrared fluorophore (NIRF)-labeled activity-based probes for in vivo imaging of legumain", ACS Chemical Biology, 2010, vol. 5, No. 2, pp. 233-243.
International Search Report and Written Opinion, PCT/US2012/026601, Mailed Sep. 12, 2012.
Reiser, et al., "Specialized roles for cysteine cathepsins in health and disease", The Journal of Clinical Investigation, vol. 120, No. 10, Oct. 2010, pp. 3421-3431.
Gounaris, et al., "Live imaging of cysteine-cathepsin activity reveals dynamic of focal inflamation, angiogenesis, and polyp growth", PLosOne, Aug. 2008, vol. 3, Issue 8, 9 pages.
Brak, et al., "Nonpeptidic tetrafluorophenoxymethyl ketone cruzain inhibitors as promising new leads for chagas disease chemotherapy", J. Med. Chem., 2010, 53, 1763-1773.

* cited by examiner

*Primary Examiner* — Michael G Hartley
*Assistant Examiner* — Jagadishwar Samala
(74) *Attorney, Agent, or Firm* — David J. Aston; Bozicevic, Field & Francis LLP

(57) ABSTRACT

Methods and materials for the imaging of cells and tissues containing active proteases such as cathepsin are disclosed. The present materials include activity based probes that bind to an enzyme and are subsequently cleaved. Cleavage results in covalent attachment of a fluorescent signal to a target protease due to removal of a quenching group which, when present on the probe causes altered or no fluorescence. The probes are non-peptidic, small molecule scaffolds linked to a reactive acyloxymethyl ketone group, a fluorophore and a quencher. The probes are cell permeable and may use, for example, a QSY21 (CAS 304014-13-9) quencher and a cyanine dye. The probes form covalent bonds with the active site of cysteine cathepsins, proteases that are upregulated at the tumor boundaries with normal tissue and at sites of inflammation.

31 Claims, 14 Drawing Sheets

GB123 (4), R=A
GB137 (5), R=B
GB119 (6), R=C

Cy5 Fluorophore        QSY21 Quencher

NON-PEPTIDIC QUENCHED FLUORESCENT IMAGING PROBES

CROSS-REFERENCE TO RELATED APPLICATIONS

This application claims priority from U.S. Provisional Patent Application No. 61/447,526 filed on Feb. 28, 2011, which is hereby incorporated by reference in its entirety and is a U.S. national stage application of PCT/US2012/026601, which is also incorporated herein by reference in its entirety.

STATEMENT OF GOVERNMENTAL SUPPORT

This invention was made with Government support under contract EB005011 awarded by the National Institutes of Health. The Government has certain rights in this invention.

REFERENCE TO SEQUENCE LISTING, COMPUTER PROGRAM, OR COMPACT DISK

None.

BACKGROUND OF THE INVENTION

1. Field of the Invention

The present invention relates to the field of compounds reactive with active proteases useful for imaging cells and organisms and binding specifically to active (but not inactive) proteases, such compounds being termed in the field "activity based probes."

2. Related Art

Background

Proteases play fundamental roles in the control of both normal and disease processes. Alterations in protease expression and activity patterns underlie many human pathological processes including cancer, arthritis, osteoporosis, atherosclerosis, and neurodegenerative disorders. Thus, a detailed understanding of how, when and where a particular protease functions in a complex cellular environment is required to better understand its role in the promotion of disease. Perhaps the most powerful way to address these issues is to develop methods that allow dynamic imaging of protease activity within a living cell or organism. Protease activity is tightly regulated in both normal and disease conditions. Therefore, it is often difficult to monitor the dynamic nature of this regulation in the context of a live cell or whole organism.

Recently, a number of elegant methods have been developed to image enzymatic activities using both invasive and whole body imaging methods (1). Virtually all of these methods make use of reporter substrates that when processed by a given enzyme target produce a signal that can be visualized using common imaging modalities. While these methods have clearly paved the way for the application of activity based reporters to diagnostic medicine, they suffer from several features such as lack of specificity and cell permeability, as well as rapid diffusion that may limit their use in high-resolution studies of enzyme regulation and localization.

Activity based probes (ABPs) are small molecules that modify a defined set of enzyme targets based on their ability to form specific covalent bonds with key catalytic residues (2-6). Since this labeling reaction is mechanism-based and requires enzyme activity, extent of probe modification serves as an indirect readout of activity levels within a given sample. Probes can be designed to target a number of different classes of enzymes through optimization of both reactive functional groups and the scaffolds used to carry the reporter tag. In the past five years, a number of new classes of ABPs have been developed and used to dissect the function of various enzyme families. The most well-established and heavily used probes are those that target proteolytic enzymes. ABPs that target serine and cysteine proteases have been applied to studies of protease function in processes such as parasite invasion, prohormone processing, transcriptional regulation, cataract formation, natural killer cell function, and cancer progression.

A number of ABPs carrying a range of fluorescent reporters have also been described (7-11). The fluorescent group serves as a highly sensitive tag that enables visualization of labeled targets after their biochemical separation. Fluorescently labeled ABPs have also been used to directly image enzyme activity using microscopy techniques. It was recently demonstrated that a fluorescent ABP can be used in a mouse model for pancreatic cancer to image cysteine protease activity during multiple stages of tumor formation (10). The use of ABPs for imaging applications has the major advantage of the formation of a permanent covalent bond with the enzyme, thus allowing direct biochemical analysis of targets. However, the major limitation of these probes is their general fluorescence both when bound to an enzyme target and when free in solution. To overcome this limitation Bogyo et al. (US 20070036725 "Imaging of protease activity in live cells using activity based probes") disclosed quenched probes (qABPs) that become fluorescent only after covalent modification of a protease target. Bogyo et al. (US 20090252677, "Probes for in vivo targeting of active cysteine proteases") disclosed probes for in vivo targeting of active cysteine proteases. Herein disclosed are a new class of in vivo optical imaging contrast probes that target key tumor and inflammatory proteases. The probes disclosed herein are non-peptidic small molecule scaffolds linked to a reactive acyloxymethyl ketone functional group. Since they have non-peptidic backbone, they are more stable in vivo and have brighter fluorescent signals in vivo as compared to the earlier disclosed peptide-based probes. The term "non-peptidic" is used to distinguish other activity-based probes which contain portions that mimic several amino acid residues that present a pseudo-substrate for the protease to be bound.

BRIEF SUMMARY OF THE INVENTION

The present invention is directed to activity based probes which bind to proteases. The probes disclosed are non-peptidic, small molecule scaffolds linked to a reactive acyloxymethyl ketone (AOMK) functional group, generally illustrated as having the formula

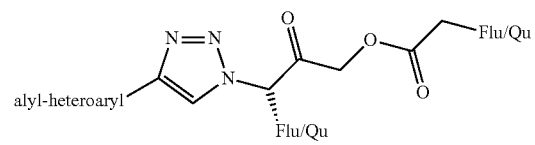

Formula A where the AOMK portion can be seen to have linkers to a fluorescent label or quencher (Flu/Qu) on two flanking positions of the AOMK, and the compound comprises a nonpeptidyl triazole portion that can have a variety of alkyl-heteroaryl substituents as described below. This structure has been incorporated into the compounds described below, and said compounds have been found to bind specifically to the protease of interest, namely cathepsin, and in particular to cathepsin B, cathepsin S, and cathepsin L. These proteases are upregulated at tumor margins and at sites of inflammation. (See e.g. Guzubbska et al., "Activity of Cathepsin B and D in Colorectal Cancer: Relationships with Tumour Budding," Anticancer Research September-October 2004 vol. 24 no. 5A 2847-2852; Serveau-Avesque et al., "Active cathepsins B, H, K, L and S in human inflammatory bronchoalveolar lavage fluids," Biol. Cell (2006) 98, 15-22).

The scaffold portion of the present compounds, comprising the AOMK group, is linked to a fluorophore for imaging purposes. The scaffold or AOMK group may also be linked to a quencher. Cleavage by the protease at the ester linkage of the AOMK group shown above separates the fluorophore from the quencher, generating a signal that remains covalently bound to the enzyme.

The present compounds are characterized by a five membered triazole ring adjacent to the AOMK warhead, a linker for a fluorophore or quencher may also be attached to the triazole ring. Hence, the probes disclosed herein are nonpeptidic, i.e. are not based on carbons linked by amide bonds, where alpha carbons carry side chains involved in enzyme recognition. The present compounds are more stable in vivo than peptide inhibitors. As a result, they have overall stronger signals including brighter fluorescent signals in vivo as compared to peptide-based probes, as shown below. The present probes can be used to assess tumor margins in vivo using either ex vivo topical administration, in vivo topical administration or in vivo systemic delivery. The compounds may be of a wide variety of structures, but may be represented generically by Formula I in claim 1.

In certain embodiments of the present compounds, no quencher is used, but a capping group is used or an end group which facilitates synthesis, such as dimethyl benzoic acid, or other substituted aryl group is used.

A wide variety of Flu/Qu pairs may be used. As is understood in the art, a given compound may be either a fluorophore or a quencher, depending on the molecule that it is paired with for purposes of energy transfer. The Flu/Qu pair is carried on the same molecule, and fluorescence results when the molecule is cleaved, separating the two. The Flu/Qu pair used herein may be a bora-diaza-indecene, such as BODIPY, and a diaryl rhodamine, such as QSY7. In one embodiment, the Flu/Qu pair is Cy5 and QSY21. Preferably, the quencher is in the portion of the molecule separated on cleavage. As is also understood in the art, a given fluorophore or quencher may be obtained commercially, and may, in that form, contain a linking portion. Alternatively, a linker may be added to a fluorophore or quencher for attachment to the molecule during the syntheses described below.

In one aspect of the present invention, specific linkers have been found to be more stable in vivo and are incorporated to link a fluorophore or quencher to the leaving end of the AOMK group, i.e., a group which binds to an enzyme and is thereby cleaved. Such linkers include alkyl groups such as isobutyric acid and aryl groups such as dimethyl benzyl or methoxy benzyl groups.

The quencher is bound via a linker which may be lower alkyl, e.g., pentyl; n is one to ten.

The present compounds may be of the following representative formulas:
A compound according to Formula I below

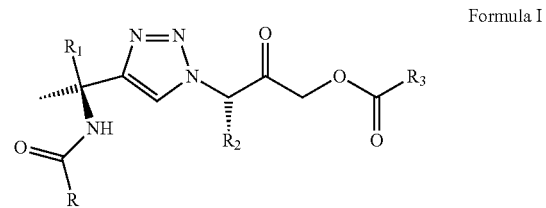

Formula I where
R is selected from the group consisting of a 4-7 member aromatic or cycloalkyl ring having therein 0 to 5 heteroatoms which are one or more of N, O, S, Si, B or Ar and may comprise a linked fluorophore or quencher;
R1 is lower alkyl;
R2 is selected from the group consisting of lower alkyl, alkoxy, alkyl amine and alkyl amide and may comprise a linked fluorophore or quencher;
R3 is selected from the group consisting of aryl (including dimethyl phenyl and 2,6 dimethyl phenyl, lower alkyl, alkoxy, alkyl amine and alkyl amide, and may comprise a linked fluorophore or quencher; and
said fluorophore and said quencher are present either as (i) only a fluorophore on one or more of R1, R2 or R3; or (ii) a fluorophore and a paired quencher where one member of the pair is on either or both of R, R1 or R2 and the other member of the pair is on R3.
R may also be selected from the group consisting of where * indicates a point of attachment of the bond shown in Formula I.

Formula II wherein R2 is a linker to Flu/Qu selected from the group consisting of lower alkyl, lower alkoxy, lower alkyl amine and lower alkyl amide; or R2 is a capping group if Qu is absent; and R4 is H or Flu/Qu.

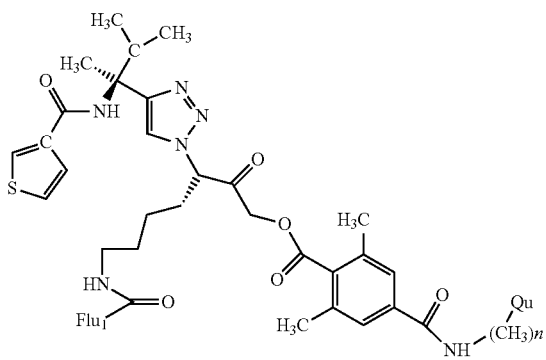

Formula III wherein n is between 1 and 5 and Flu1 and Qu are a fluorophore-quencher pair.

In the above formulas, R3 of Formula I is shown as a 2,6 dimethyl phenyl group with a 4 linker group to a quencher. In other embodiments, e.g. Formula II, it may be a capping group derived from benzyloxycarbonyl or dimethyl benzoic acid.

Also, the Flu/Qu pair may be a bora-diaza-indecene and a diaryl rhodamine, respectively; cyanine and QSY; and/or, in a specific embodiment, Flu1=Cy5 and Qu=QSY21.

The present invention also comprises methods of imaging using the quenched activity based probes. Such methods include a method of imaging tumor margins in a living organism, comprising:

(a) administering to said organism a cathepsin activity-based probe according to Formula I or III for binding to a predetermined protease, wherein the fluorophore and quencher in said Formula I or III separate upon binding and cleavage by the protease;

(b) exposing said organism to electromagnetic radiation which excites non-quenched fluorophore to produce a detectible signal; and (c) detecting said signal and creating an image thereby.

The methods may be applied to cellular, animal and medical studies. The probes may be administered by intravenous injection, direct injection to a specific site, topically, and other means. Since protease activity is associated with tumor invasiveness and metastasis, the method has particular applicability to imaging a solid tumor, such as in breast cancer, which may be modeled by MCF-10A cells and other known model cell lines.

The present compounds have been found to specifically bind cathepsin S, cathepsin B, and cathepsin L, in that order of activity (as shown by the gels in FIG. 6)

The fluorescence may be selected to be in the range of about 580-720 nm to take advantage of the relative transparency of tissue to IR light.

Also, the use of a spectral imager with the present methods has been found to provide improved resolution and sensitivity.

BRIEF DESCRIPTION OF THE DRAWINGS

FIG. 10A shows that tumor fluorescence and background fluorescence were measured and the tumor to background ratio was determined, as shown in FIG. 10C. The final time point is shown in the images in FIG. 10C. The overall probe signal is dramatically higher for BMV083 (10C, left image) compared to GB137 (10C, right image). Moreover, the signal to background ratio is enhanced with BMV083.

DETAILED DESCRIPTION OF THE PREFERRED EMBODIMENTS

Introduction

Figure 1:
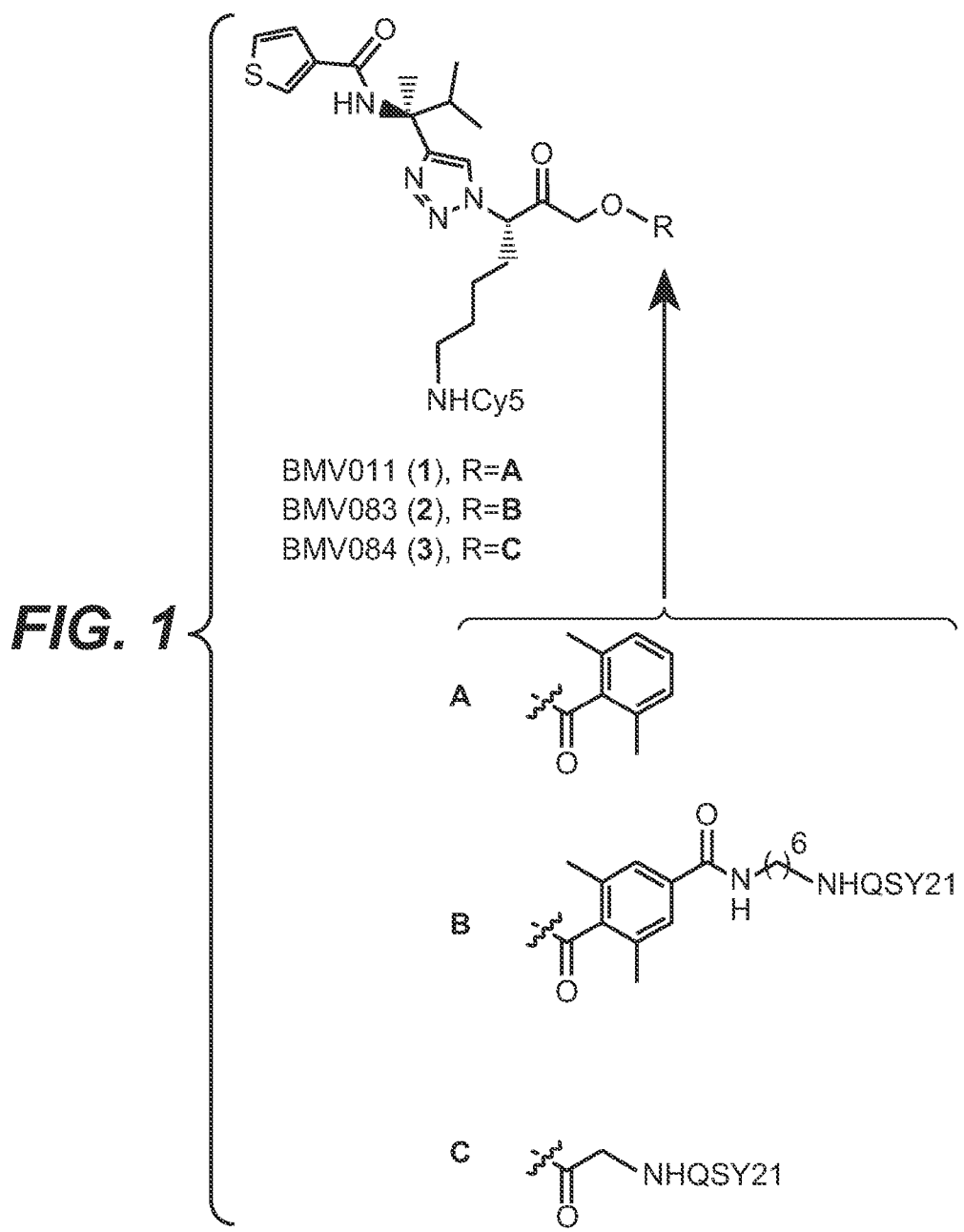
FIG. 1 is a drawing of exemplary compounds BMV011 (compound 1), BMV083 (compound 2) and BMV 084 (compound 3), where R varies as to the quencher group, there being none in A, QSY21 (a commercially available quencher) linked through an alkyl-dimethyl benzoic amide in B, and a methyl group in C. The structure of QSY 21 is shown below.

Described below is a series of quenched and unquenched activity based probes (qABPs) that become fluorescent upon cleavage resulting from activity-dependant covalent modification of a protease target. These reagents freely penetrate cells and allow direct imaging of protease activity in living cells. Targeted proteases are directly identified and monitored biochemically by virtue of the resulting covalent tag thereby allowing unambiguous assignment of protease activities observed in imaging studies. Further described is the design and synthesis of a selective, cell permeable qABP for the study of cysteine cathepsins. The probes disclosed herein are used to monitor real-time protease activity in living cells and organisms using fluorescence microscopy techniques as well as standard biochemical methods. The probes target key tumor and inflammatory proteases. These probes can be applied topically to tissues removed from patients (ex vivo topical), by direct topical application onto tissues in a patient (in vivo topical) or by direct injection IV or possibly by oral routes (in vivo systemic). They would allow assessment of tumor location and margins for early detection of tumors and also to assist surgical removal of tumor tissues. They could also be used to detect other types of inflammation associated with conditions such as cancer, atherosclerosis, arthritis and any other pathology mediated by inflammation. Proteases to be monitored in the cysteine cathepsin family include cathepsins B, C (also known as cathepsin J and dipeptidyl-peptidase 1), F, H, K (also known as cathepsin O2), L, O, S, W, V (also known as cathepsin L2), and Z (also known as cathepsin X and cathepsin P).

Cysteine cathepsins are a family of lysosomal proteases that are often upregulated in various human cancers, and have been implicated in distinct tumorigenic processes such as angiogenesis, proliferation, apoptosis and invasion. The cysteine cathepsin family constitutes the largest cathepsin family, with 11 proteases in humans referred to as clan CA, family C1a: cathepsins B, C (also known as cathepsin J and dipeptidyl-peptidase 1), F, H, K (also known as cathepsin O2), L, O, S, W, V (also known as cathepsin L2), and Z (also known as cathepsin X and cathepsin P).

During cancer progression, cathepsins are often translocated to the cell surface of tumor cells or are secreted into the extracellular milieu, where they can promote tumor invasion through several possible mechanisms. First, they can directly cleave components of the extracellular matrix and basement membrane, essentially clearing a path for the migration of tumor cells away from the primary tumor mass. Second, at the cell membrane, cathepsins can direct a proteolytic cascade in which they activate other proteases such as matrix metalloproteinases and urokinase plasminogen activator, which in turn promote invasion. Finally, cleavage of the cell adhesion protein, E-cadherin, at the cell surface can disrupt adherens junctions and thus facilitate cancer cell migration and invasion. Therefore, cathepsins are emerging as major players in tumor progression, making them potential drug targets for a wide range of human cancers. In particular, cathepsin B as used here and generally understood, refers to EC 3.4.221; cathepsin S refers to EC 3.4.22.27; and cathepsin L refers to EC 3.4.22.15. The present compounds, in certain embodiments are useful in specifically inhibiting one or more of these enzymes in humans.

Definitions and Abbreviations

Abbreviations

NMM—N-methyl morpholine, IBCF—Isobutylchloroformate, HBr—hydrogen bromide, TFA—trifluoroacetic acid, DIEA—Diisopropylethylamine, qABP—quenched activity based probe, AOMK—acyloxymethyl ketone.

The terms "activity based probe" and "warhead" are used here according to their accepted meanings, namely compound which is an enzyme inhibitor which acts by binding to a specific enzyme and inactivating through chemical modification (typically covalent binding) to the active site of the enzyme. The portion of the activity-based probe (ABP) that chemically binds to the enzyme is termed the "warhead." The warhead is attached to a pseudosubstrate, i.e., a non-peptidic small molecule scaffold. The enzyme acts on proteins and is typically a protease with a specific recognition sequence. Thus the term warhead includes AOMK, epoxy, nitrile and other known reactive groups. The remainder of the molecule contains 1-3 amino acid or amino acid-like residues. Further clarification of these terms may be found in U.S. Pat. No. 6,777,403 to Cheronis, issued Aug. 17, 2004, entitled "Method and structure for inhibiting activity of serine elastases."

The term "alkyl", alone or in combination with other groups, refers to a branched or straight-chain monovalent saturated or unsaturated (i.e. including unless otherwise specified alkenyl or alkynyl) hydrocarbon radical of one to twenty carbon atoms, preferably one to sixteen carbon atoms, more preferably one to ten carbon atoms. The term "lower alkyl", alone or in combination with other groups, refers to a branched or straight-chain monovalent alkyl radical of one to ten carbon atoms, preferably one to four or one to eight carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like. Preferable lower alkyl residues are methyl and ethyl, with methyl being especially preferred. The term lower alkyl, unless specified as unsubsituted, includes substituted alkyl, such as "perfluoro-lower alkyl", which refers to a lower alkyl group wherein all of the hydrogens of the lower alkyl group are substituted or replaced by fluoro. Also included unless otherwise specified are "alkoxy", which the group R'—O—, wherein R' is alkyl. The term "lower-alkoxy" refers to the group R"—O—, wherein R" is lower-alkyl. Examples of lower alkoxy groups are e.g., methoxy, ethoxy, propoxy, isopropoxy, butoxy, isobutoxy and hexyloxy, with methoxy being especially preferred. Also included unless otherwise specified is "lower alkylthio", which refers to the group R'—S—, wherein R' is lower-alkyl as defined above. Also included unless otherwise specified are alkyl amine, ie. a straight or branched, saturated or unsaturated, molecule having 1-10 or more carbon atoms and one or more amino groups. The alkyl portion of the alkyl amine can be methyl, ethyl, propyl, butyl, pentyl, hexyl, iso-propyl, iso-butyl, sec-butyl, tert-butyl, etc. The term alkyl amide denotes an acyl radical attached to an amine or monoalkylamine, wherein the term acyl has a standard meaning as comprising RCO—. Examples of "alkylamide" include acetamido, propionamido and the like.

The term "aryl" refers to an aromatic monovalent mono- or polycarbocyclic radical, such as phenyl and naphthyl, preferably phenyl. Substituted aryl is aryl that is mono-, di- or tri-substituted, independently, by lower alkyl, lower alkoxy, halogen, amino or perfluoro-lower alkyl, preferably by lower alkyl, lower alkoxy and halogen. Exemplary aryl groups are methyl phenyl, di- and trimethyl phenyl, and various lower alkyl mon- di- and tri-substituted phenyl, where the aryl group is linked to the scaffold through an alkyl or other linker.

The present compounds may be made through the use of solid phase peptide synthesis techniques, which will employ known protective groups, capping groups, and the like. The term "capping group" refers to group has the effect of preventing further chemical reactions from occurring at that site, and is a non-amino acid moiety bonded to the C- or N-terminal of the peptide chain. Examples of common N-terminal capping groups used in peptide synthesis are Boc (t-butoxycarbonyl) and Cbz (benzyloxycarbonyl). Other capping groups useful in synthesis are acetyl and adamantyl, dimethyl benzyl succinimidyl, 4-methylbenzyl, 2-thiophenylmethyl, 4-thiazolylmethyl, 3,5-difluorobenzyl, etc.

The term "cycloalkyl" refers to cyclic alkyl groups of from 3 to 14 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The term "heterocycloalkyl" refers to cyclo alkyl groups having one or more heteroatoms, e.g. N, O, or S. Heterocycloalkyl refers to a stable 4-14 membered monocyclic or multicyclic ring, wherein at least one of the rings contains at least one heteroatom and wherein there are no aromatic rings. Heterocycloalkyl is meant to include multicyclic rings, wherein one ring contains a heteroatom and another ring does not contain a heteroatom. Non-limiting examples of heterocycloalkyl include piperadinyl, piperazinyl, furanyl, prrolidinyl, morpholinyl.

"(4-6 membered) heterocycloalkyl" is a subset of heterocycloalkyl and refers to a stable 4-6 membered monocyclic ring containing at least one heteroatom and wherein there are no aromatic rings. Exemplary heterocycloalkyl groups include piperadinyl, piperazinyl, furanyl, prrolidinyl, morpholinyl. "(4-6 membered) heterocycloalkyl" is a subset of heterocycloalkyl and refers to a stable 4-6 membered monocyclic ring containing at least one heteroatom and wherein there are no aromatic rings.

The phrase "in purified form" in reference to a compound means that the compound has been essentially isolated from contaminants and other possibly active ingredients. It does not require absolute purity, but at least purification and recovery as commonly practiced in organic synthesis.

Figure 2:
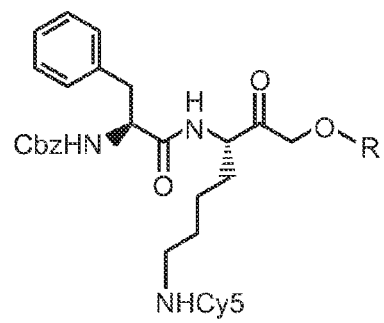
FIG. 2 is a drawing of control compounds GB123, GB137 and GB119, with the corresponding groups A, B and C (compounds 4-6) fluorescent imaging probes. The structures of the Cy5 fluorophore and the QSY21 quencher shown as "Cy5" and "QSY21". "R" in this Figure and FIG. 1 corresponds to C(=O)—R3-Flu/Qu in Formula I below. Cbz=carboxybenzyl.
Figure 2:
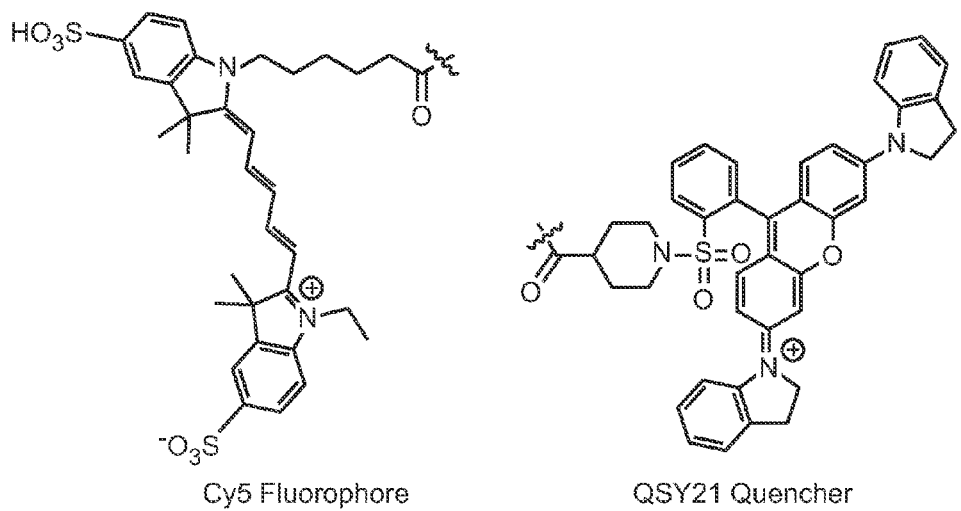

The terms "Flu, Ou and Flu/Ou" refers to, respectively, a fluorophore, a quencher, or a fluorphore/quencher pair. Particular fluorophores such as bora-diaza-indence, rhodamine, and cyanine are described in detail below. The term quencher has meaning with reference to a particular quencher, as also explained below, and denoted by the term Flu/Qu, where either a fluorophore or a quencher can be linked at a given position on the molecule. For example, Flu/Qu may refer to Cy5, as shown in FIG. 2. As shown there, a carboxy group is used for coupling, and may be coupled to the amine as shown in FIG. 1. However, for added clarity, a known embodiment of Cy5 is represented below:

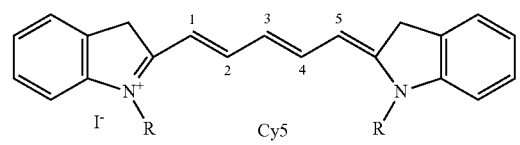

It can be seen that in this representation of the Cy5 dye, the "R" groups can be in a variety of linker structures, such as the 6 carbon linker shown in FIG. 2. Such linkers are well known in the art and included in the fluorophore or quencher as represented by Flu or Qu. It is understood that if only a single instance of an Flu/Qu is in a compound, it will function as a fluoresescer. It is preferred that the Flu/Qu be paired, so that fluorescence indicates binding and cleavage of the molecule by the protease.

Compound Synthesis

An exemplary synthetic scheme for compounds BMV 083, BMV 011 and BMV 084 is given in FIG. 4. The compounds synthesized according to FIG. 4 contain the core structure,

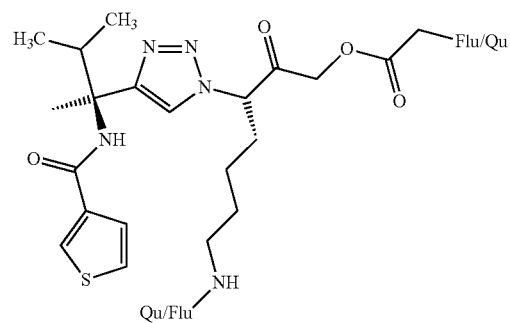

where Qu/Flu and Flu/Qu can be a variety of fluorophores and quenchers, including linkers to the illustrated structure. Qu/Flu and Flu/Qu are paired so that one is a fluorophore and one is a quencher. In the case of BMV011, Flu/Qu is Cy5 for the fluorophore and the quencher is replaced by a dimethyl benzyl group. As noted in FIG. 3, the thiophene group illustrated can be replaced with a variety of heteroaryl or heteroalkyl groups, such as heteromonocyclic groups, further exemplified by piperzine or morpholino groups as illustrated below:

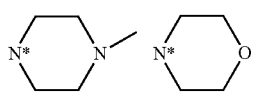

Variations in the illustrated synthesis to form other compounds as described below will be readily apparent to those skilled in the art of organic synthesis. For further synthetic methods, one may consult Kato, D., Boatright, K. M., Berger, A. B., Nazif, T., Blum, G., Ryan, C., Chehade, K. A. H., et al. (2005). Activity-based probes that target diverse cysteine protease families. *Nature Chemical Biology*, 1(1), 33-38, or Brak et al J. Med. Chem 2010 53, 1763-1773, which discloses synthesis for the building blocks necessary to do the CLICK reaction.

Quenchers and Fluorophores

The term "fluorophore" means a fluorescent molecule, i.e., one that emits electromagnetic radiation, especially of visible light, when stimulated by the absorption of incident radiation. The term includes fluorescein, one of the most popular fluorochromes ever designed, which has enjoyed extensive application in immunofluorescence labeling. This xanthene dye has an absorption maximum at 495 nanometers. A related fluorophore is Oregon Green, a fluorinated derivative of fluorescein. The term further includes bora-diaza-indecene, rhodamines, and cyanine dyes. The term further includes the 5-EDANS (Nucleotide analogs adenosine 5'-triphosphate [g]-1-Naphthalenesulfonic acid-5(2-Aminoethylamide) (ATP[g]-1,5-EDANS) and 8-Azidoadenosine 5'-triphosphate [g]-1-Naphthalenesulfonic acid-5(2-Aminoethylamide) (8N3ATP[g]-1,5-EDANS).

The term "bora-diaza-indecene" means compounds represented by 4,4-difluoro-4-bora-3a,4a-diaza-s-indacene, known as BODIPY® dyes. Various derivatives of these dyes are known and included in the present definition, e.g., Chen et al. "4,4-Difluoro-4-bora-3a,4a-diaza-s-indacene (BODIPY) dyes modified for extended conjugation and restricted bond rotations," J Org Chem. 2000 May 19; 65(10):2900-6. These compounds are further defined in reference to the structures set out below under the heading "FLUOROPHORES." In the exemplified BODIPY TMR-X, R1 in fluorophores=benzyl methoxy; the structure is further shown in Scheme 1. The linker is an amide bond to the lysine side chain chosen as part of the dipeptide starting material.

The term "rhodamine" means a class of dyes based on the rhodamine ring structure. Rhodamines include (among others): Tetramethylrhodamine (TMR): a very common fluorophore for preparing protein conjugates, especially antibody and avidin conjugates; and carboxy tetramethyl-rhodamine (TAMRA) used for oligonucleotide labeling and automated nucleic acid sequencing. Rhodamines are established as natural supplements to fluorescein based fluorophores, which offer longer wavelength emission maxima and thus open opportunities for multicolor labeling or staining. The term is further meant to include "sulfonated rhodamine," series of fluorophores known as Alexa Fluor dyes.

The dramatic advances in modern fluorophore technology are exemplified by the Alexa Fluor dyes introduced by Molecular Probes (Alexa Fluor is a registered trademark of Molecular Probes). These sulfonated rhodamine derivatives exhibit higher quantum yields for more intense fluorescence emission than spectrally similar probes, and have several additional improved features, including enhanced photostability, absorption spectra matched to common laser lines, pH insensitivity, and a high degree of water solubility. Also related to rhodamine dyes is TAMRA.

The term "cyanine" means a family of cyanine dyes, Cy2, Cy3, Cy5, Cy7, and their derivatives, based on the partially saturated indole nitrogen heterocyclic nucleus with two aromatic units being connected via a polyalkene bridge of varying carbon number. These probes exhibit fluorescence excitation and emission profiles that are similar to many of the traditional dyes, such as fluorescein and tetramethylrhodamine, but with enhanced water solubility, photostability, and higher quantum yields. Most of the cyanine dyes are more environmentally stable than their traditional counterparts, rendering their fluorescence emission intensity less sensitive to pH and organic mounting media. In a manner similar to the Alexa Fluors, the excitation wavelengths of the Cy series of synthetic dyes are tuned specifically for use with common laser and arc-discharge sources, and the fluorescence emission can be detected with traditional filter combinations.

Marketed by a number of distributors, the cyanine dyes are readily available as reactive dyes or fluorophores coupled to a wide variety of secondary antibodies, dextrin, streptavidin, and egg-white avidin. The cyanine dyes generally have broader absorption spectral regions than members of the Alexa Fluor family, making them somewhat more versatile in the choice of laser excitation sources for confocal microscopy.

The term "quencher" means a compound that modulates the emission of a fluorophore. A quencher may itself be a fluorescent molecule which emits fluorescence at a characteristic wavelength. Thus, a fluorophore may act as a quencher when appropriately coupled to another dye and vice versa. In this case, increase in fluorescence from the acceptor molecule, which is of a different wavelength to that of the donor label, will also indicate binding of the ABP. Alternatively, the acceptor does not fluoresce (dark acceptor): Such acceptors include DABCYL, methyl red, QSY-7 diarylrhodamine dyes and 6-(dimethylamino)-2-[4-[4 (dimethylamino)phenyl]-1,3-butadienyl]-1-ethyl quinolinium perchlorate (CAS number 181885-68-7). Typical fluorophore/quencher compounds include certain rhodamine dyes or Cy5.

The term "aryldiazo" refers to quenching compounds such as 4 (4'dimethylaminophenylazo) benzoic acid (DABCYL), a common dark quencher used widely in many assays, such as "molecular beacons" for DNA detection (U.S. Pat. No. 5,989, 823).

Diazo dyes of the BHQ series, which are referred to as "Black Hole Quenchers" (International Patent Publication No. WO 01/86001), provide a broad range of absorption which overlaps well with the emission of many fluorophores. The QSY series dyes from Molecular Probes are another series of dark quenchers used extensively as quenching reagents in many bioassays (U.S. Pat. No. 6,399,392).

The structure of QSY 7 is illustrated in Sriram Kumaraswamy et al., US Patent Publication 2005/0014160, "Assays for protease enzyme activity." QSY-7 is a nonfluorescent diarylrhodamine derivative.

QSY21 is a nonfluorescent diarylrhodamine chromophore with strong absorption in the visible spectrum, and is an effective fluorescence quencher.

Fluorophore/quencher pairs are further illustrated in Lee, "Detection System," United States Patent Application 20040241679, published Dec. 2, 2004.

Linkers

Both quenchers and fluorophores, as referred to herein, include linkers. That is, the terms Flu and Qu as used below, should be understood to include a variety of linking groups, including lower alkyl, cycloalkyl and heterocycloalkyl linking groups that extend from the active fluorophore or quencher to the core structure where the Flu or Qu is attached. Generally, preferred linkers have from 20 to 40 bonds from end to end, preferably 25 to 30 bonds, and may be branched or straight chain or contain rings. The bonds may be carbon-carbon or carbon-heteroatom or heteroatom-heteroatom bonds. The linkage can be designed to be hydrophobic or hydrophilic. The linking group can contain single and/or double bonds, 0-10 heteroatoms (O, S preferred), and saturated or aromatic rings. The linking group may contain groupings such as ester, ether, sulfide, disulfide and the like.

Exemplary Fluorophores

BODIPY® analogs (4,4-difluoro-4bora-3a,4a-diaz-s-indacene) analogs

R1=H, CH3, C6H5, C4H3X (X=S, NH), C6H4OCH3, (CH=CH)C6H5, (CH=CH)2C6H5, CH2CH2COOH, CH2CH2CO—

R2=H, Br

R3=H, CH3, C6H5

R4=H, CH2CH2CO—

R5=H, CH3

R6=H, Br, CH2CH2CONH(CH2)5CO—

R7=H, CH3, (CH2)2CO—, (CH2)2COOH, C6H4OCH2CONH(CH2)5CO—, (CH2)4CO—, CH2CH2CONH(CH2)5CO—, CH2CH2CONHCH(CH2SO3-)CO—

Fluorescein Derivatives

R1, R2=H, CO—, COOH,

CONH(CH2)5CO—, NHCOCH2SCH2CH2CO—, F, N(CH3)2, N(CH3CH2)2, SO2NH(CH2)5CO—, SO3-

R3, R8=F, Br, Cl, I, CH3, OCH3

R4=O, NHCOCF3, NH2, NHCH2CH3

R5,R6=Br, Cl, SO3-

R7=O, OCOCF3, NHCOCF3, NH2, NHCH2CH3

R9=COOH, SO3-, SO3H, SO2NH(CH2)5CO

R10=Cl

DANSYL (5-dimethylaminonaphthalene)

R1=CO—, SO2-, SO2NH—

Alexa Fluors

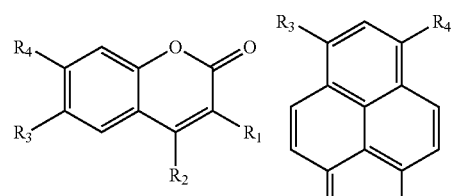

Alexa Fluor 350

Alexa Fluor 405

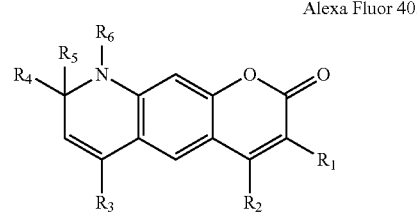

Alexa Fluor 430

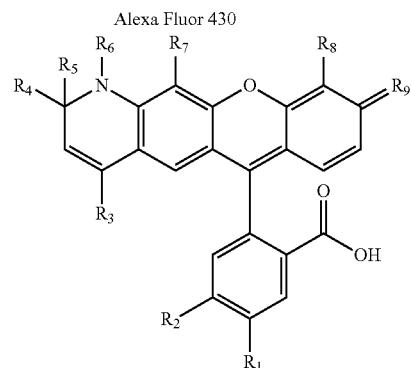

Alexa Fluor 514

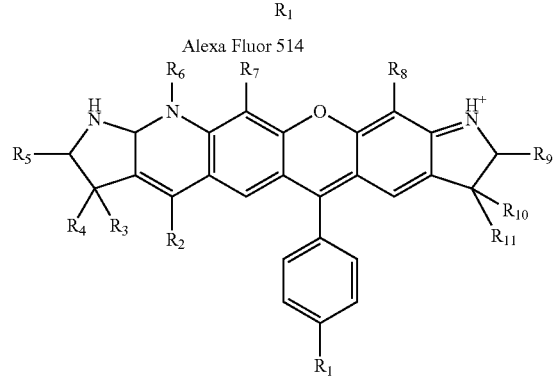

Alexa Fluor 532

Alexa Fluor 546, 568, 594, 610

R=H, CH3, SO3-, CF3 CH2SO3-, CH2SO3H, (CH2)5, SO3, Cl, SCH2CONH(CH2)5CO—, CO—

Cy Fluorophores

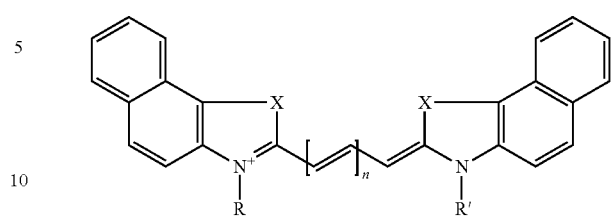

X=O, NR, C(CH3)2, S, Se
R, R'=alkyl aryl
n=0-5

Exemplary Quenchers

QSY quenchers

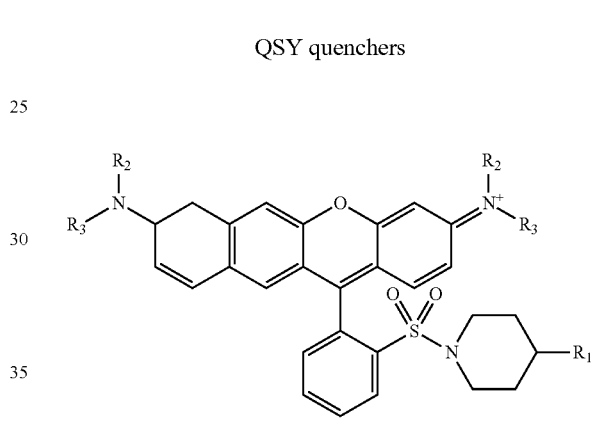

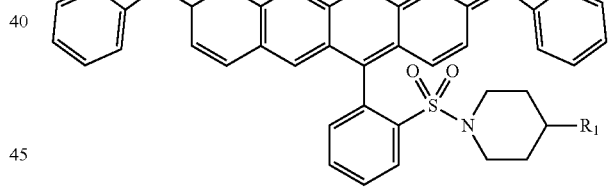

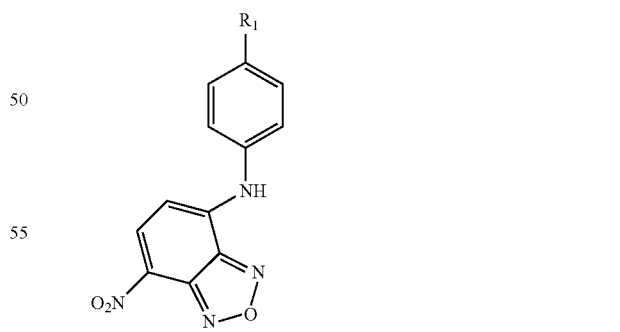

R1=CO—, CONH—, CONH(CH2)5NH—, (CH2)5CO—, CONH(CH2)5CO—, CH2NHCO—

R2, R3=CH3, C6H5, C6H4SO3+

QSY 21 quencher, as obtained from Invitrogen, QSY® 21 carboxylic acid, succinimidyl ester, has the following structure:

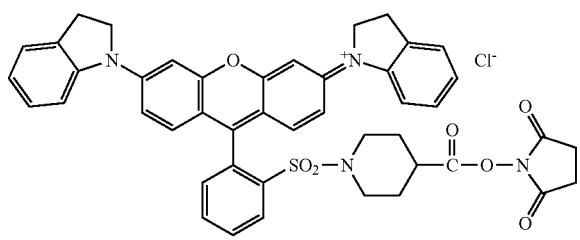 [SMILES: O=C(ON1C(=O)CCC1=O)C1CCN(S(=O)(=O)c2ccccc2-c2c3cc/c(=[N+]4/CCc5ccccc54)cc-3oc3cc(N4CCc5ccccc54)ccc23)CC1 ; [Cl-]]

The succinimidyl ester facilitates the linkage of the quencher to a linking group on the compound to be labeled.
Others:

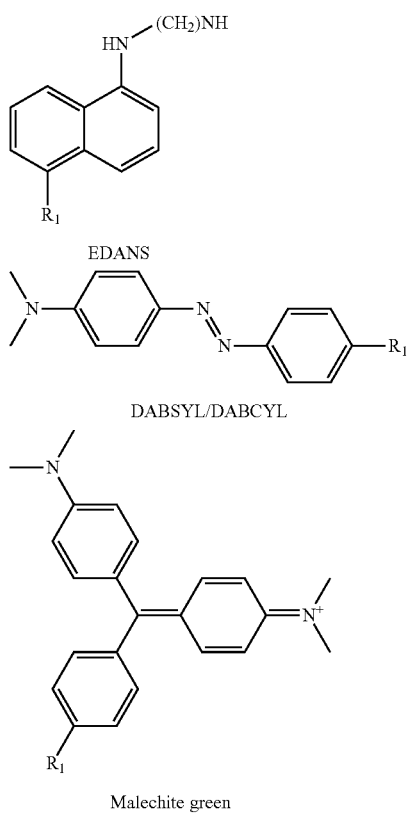

R1=CO—, SO2-, SO2NH—,

Choice of Fluorophore and Quencher Pairs for Imaging

As described, a wide variety of fluorophores and quenchers are available for use with the present ABPs. The fluorophore and the quencher must be appropriately paired so that a detectible signal is generated when the probe binds to the protease and is cleaved. One may employ principles learned from FRET imaging to choose appropriate molecular pairs that will yield clear signals.

FRET, or fluorescence resonance energy transfer, is the non-radiative transfer of photon energy from a donor fluorophore to an acceptor fluorophore when both are located within close proximity (1-10 nm). Using FRET one can prepare a qABP with a donor and acceptor on portions of the molecule that physically separate when the probe binds to the protease target. Before cleavage, when the donor fluorophore is excited by light it transfers its excited state energy to a light absorbing molecule (the acceptor). This transfer of energy is non-radiative, due primarily to a dipole-dipole interaction between donor and acceptor. Thus in choosing appropriate pairs, one would consider the following prerequisites:

1. The donor's fluorescence emission spectrum overlaps (to some extent) the excitation spectrum of the acceptor
2. The donor fluorescence has a sufficiently long lifetime (ns)
3. The donor and acceptor dipole orientations must be approx. parallel
4. The distance between donor and acceptor is small (about 1-10 nm)

A great many fluorophores have been examined for FRET. A review of FRET principles is found in Selvin, "The renaissance of fluorescence resonance energy transfer," *Nature Structural Biology* 7(9), 730-734 (2000).

An excellent overview of FRET including the conditions for FRET and the FRET equation is available online from the Molecular Probes Handbook of Fluorescent Probes and Research Products at http://probes.invitrogen.com/handbook.

Primary Conditions for FRET (from the Molecular Probes Handbook) include the following: Donor and acceptor molecules must be in close proximity (typically 10-100 Å, which is 1-10 nm. For comparison the diameter of a DNA double helix is 2.3 nm, an F-actin filament ~6 nm, an intermediate filament ~10 nm, and a microtubule 25 nm).

Absorption spectrum of the acceptor must overlap fluorescence emission spectrum of the donor. Donor and acceptor transition dipole orientations must be approximately parallel (for optimal energy transfer).

In standard FRET imaging one excites the donor fluorophore with excitation light, and collects sequentially the fluorescence emission of the donor and acceptor. For the donor-acceptor pair of fluorescein-rhodamine one might use a 470-490 nm excitation filter, and a 500-520 nm emission filter for collecting the light from the fluorescein donor. One might then use a 600-650 nm emission filter for collecting the light from the rhodamine acceptor. These emission filters need to collect just the shorter wavelength range of the donor, and just the long emission tail of the acceptor, to avoid cross-talk between the two image channels. That is, one would want to avoid collecting fluorescein emission in the rhodamine channel and vice versa. The problem is that for FRET to work, the donor emission and acceptor excitation spectra must overlap (high overlap is good), but for good signal-to-noise ratio imaging one must avoid collecting the "wrong" photons through a filter.

A potential alternative collection method is to use a spectral imaging device that would collect all the photons of both the donor and acceptor simultaneously and somehow separate out the two on the basis of their spectra. One would still excite fluorescein from 470-490 nm, but one would collect all the emission photons from 500-650 nm simultaneously. A device that should be able to do this is a fluorescence microscope with the suggested 470-490 nm/500-650 nm filter cube and an Applied Spectral Imaging, Inc., SpectraCube® spectral imaging device. The SpectraCube® is a Fourier transform interferometer spectral imaging device that attaches to a standard microscope (i.e., Axioplan-2, Axioskop-2, Eclipse E800, or their inverted microscope equivalents) by a C-mount adapter. The device collects all the photons all the time, and uses clever mathematical analyses to quantify the amount of each fluorophore by their spectra. Using an interferometer allows the device to "collect all the photons all the time" and compute the spectrum later (offline).

Compositions for Administration In Vivo

The present compounds have been shown to inhibit cathepsin B, S, and L. The potential of cathepsin inhibitors as pharmaceutical agents has been demonstrated with prototype inhibitors in several animal models. Use of inhibitors has been reported for example, in Yamada et al., "Cathepsin L Inhibition Prevents Murine Autoimmune Diabetes via Suppression of CD8+ T Cell Activity," PLoS ONE 5(9): e12894. doi:10.1371/journal.pone.0012894 and Zheng et al., "Cathepsin L inhibition suppresses drug resistance in vitro and in vivo: a putative mechanism," Am J Physiol Cell Physiol January 2009 vol. 296 no. 1 C65-C74. Cathepsin S inhibitors have been proposed for use in treating inflammatory bowel disease and autoimmune disease. Given the above-described art, one would treat an apotosis-related disease through administration of a compound as described herein, based on present in vivo data, and according to a suitable formulation as described below.

Therapeutic compositions of the present invention, as well as formulations for in vivo imaging, can be formulated in an excipient that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal,— or o-cresol, formalin and benzyl alcohol. Standard formulations can either be liquid injectables or solids, which can be taken up in a suitable liquid as a suspension or solution for injection. Thus, in a non-liquid formulation, the excipient can comprise dextrose, human serum albumin, preservatives, etc., to which sterile water or saline can be added prior to administration. One embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

Further guidance on formulation and administration of the present compounds may be obtained from U.S. Pat. No. 6,906,037 to Little, I I, et al., issued Jun. 14, 2005, entitled "Therapeutic peptide-based constructs." A formulation may be prepared having the active enzyme probe at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another stable pharmaceutical composition contains an active probe at a concentration of 2 mg/ml in 5 mM citrate, 150 mM NaCl, 0.2% poloxamer 188 and 0.002% polysorbate 80. When given parenterally, the product compositions are generally injected in doses ranging from 1 µg/kg to 100 mg/kg per day, preferably at doses ranging from 0.1 mg/kg to 20 mg/kg per day. The treatment may continue by continuous infusion or intermittent injection or infusion, at the same, reduced or increased dose per day for, e.g., 1 to 3 days, and additionally as determined by the treating physician.

Example 1

Design and Synthesis of Reactive Probes

Unless otherwise noted, all resins and reagents were purchased from commercial suppliers and used without further purifications. All solvents used were of HPLC grade. All water-sensitive reactions were preformed in anhydrous solvents and under positive pressure of argon. Reactions were analyzed by LC/MS using an API 150EX (Applied Biosystems).

Reverse-phase HPLC was conducted with an AKTA explorer 100 (Amersham Pharmacia Biotech) using C18 columns. High-resolution MS analyses were performed by Stanford Proteomics and Integrative Research Facility using a Bruker Autoflex MALDI TOF/TOF mass spectrometer. Fluorescent scanning of gel and plates were done using a Typhoon 9400 (GE Healthcare) flatbed laser scanner (Amersham Biosciences).

The exemplified embodiments below focus on the acyloxymethyl ketone (AOMK) reactive group for probe design as this "warhead" targets diverse families of cysteine proteases. More importantly, the mechanism of covalent modification of a cysteine protease by an AOMK involves the loss of its acyloxy group). Thus, a probe carrying a fluorescent reporter group on its peptide scaffold and a highly efficient quenching molecule attached to the acyloxy leaving group should result in a quenched probe that only becomes fluorescent upon covalent labeling of an enzyme target. The first generation of qABPs made use of the fluorescein/4-([4-(Dimethylamino)phenyl]azo) benzoic acid (DABCYL) pair which was shown to be effective for related applications. Unfortunately, it was found that while it was possible to use cell permeable BODIPY analogs of fluorescein, the DABCYL group prevented probes from freely entering cells (data not shown). Furthermore, it was found that direct attachment of the DABCYL quenching group to the reactive hydroxy ketone methylene resulted in probes that were highly unstable in aqueous solution and in addition showed dramatically reduced potency for target proteases, presumably due to the proximity of the bulky quencher to the active site (data not shown). Therefore, attention was shifted to the larger but potentially more cell permeable quenching group QSY-21, paired with Cy5. As discussed below, a wide variety of fluorophore-quencher pairs can be used in the present compounds, including QSY-7. The fluorophore and quencher are attached to the probe through a linker to improve stability and potency.

Synthesis of the Probe BMV011 (Compound 1, FIG. 1).

Referring now to FIG. 4, chiral intermediate 11 was synthesized according to literature procedures. (See Patterson, A. W.; Ellman, J. A. "Asymmetric synthesis of R,R dibranched propargylamines by acetylide additions to N-tertbutavnesulfinyl ketimines." *J. Org. Chem.* 2006, 71, 7110-7112).

Figure 3A:
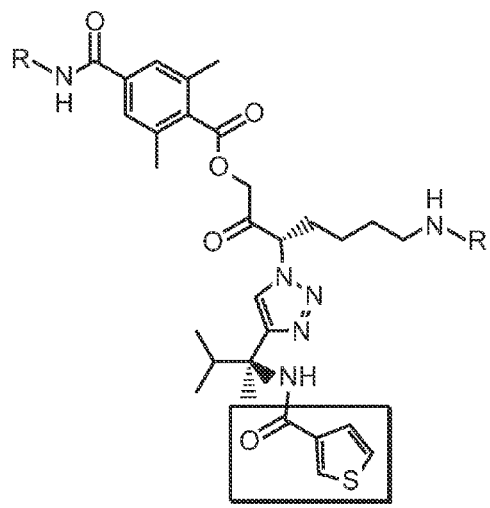
FIGS. 3A, 3B and 3C is a set of drawings showing three structures of the present compounds where R in Formula I has been varied to obtain N-terminal modifications to improve pharmacokinetic properties. The same compound is shown in each of A, B and C, with variations in the boxed area.
Figure 3B:
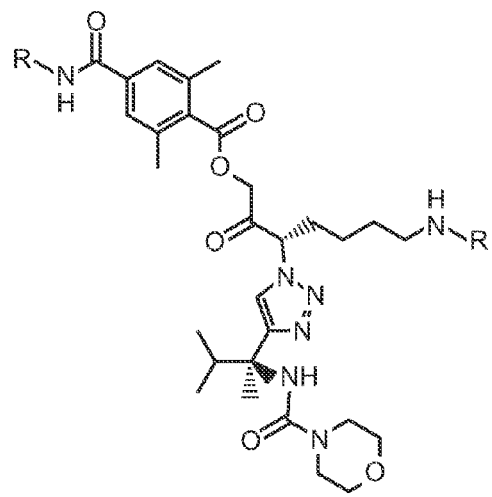
Figure 3C:
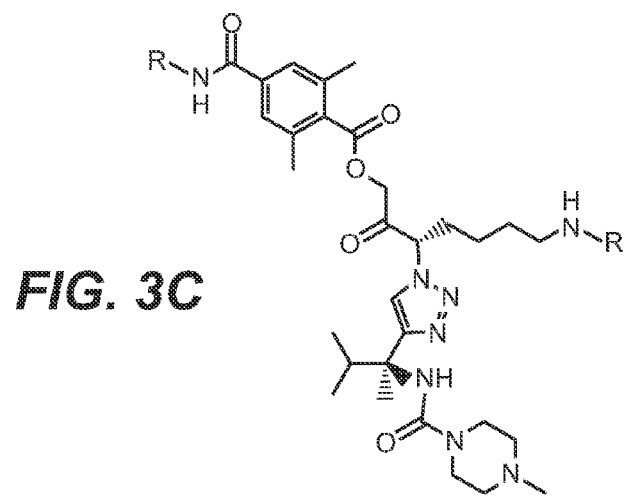
Figure 4A:
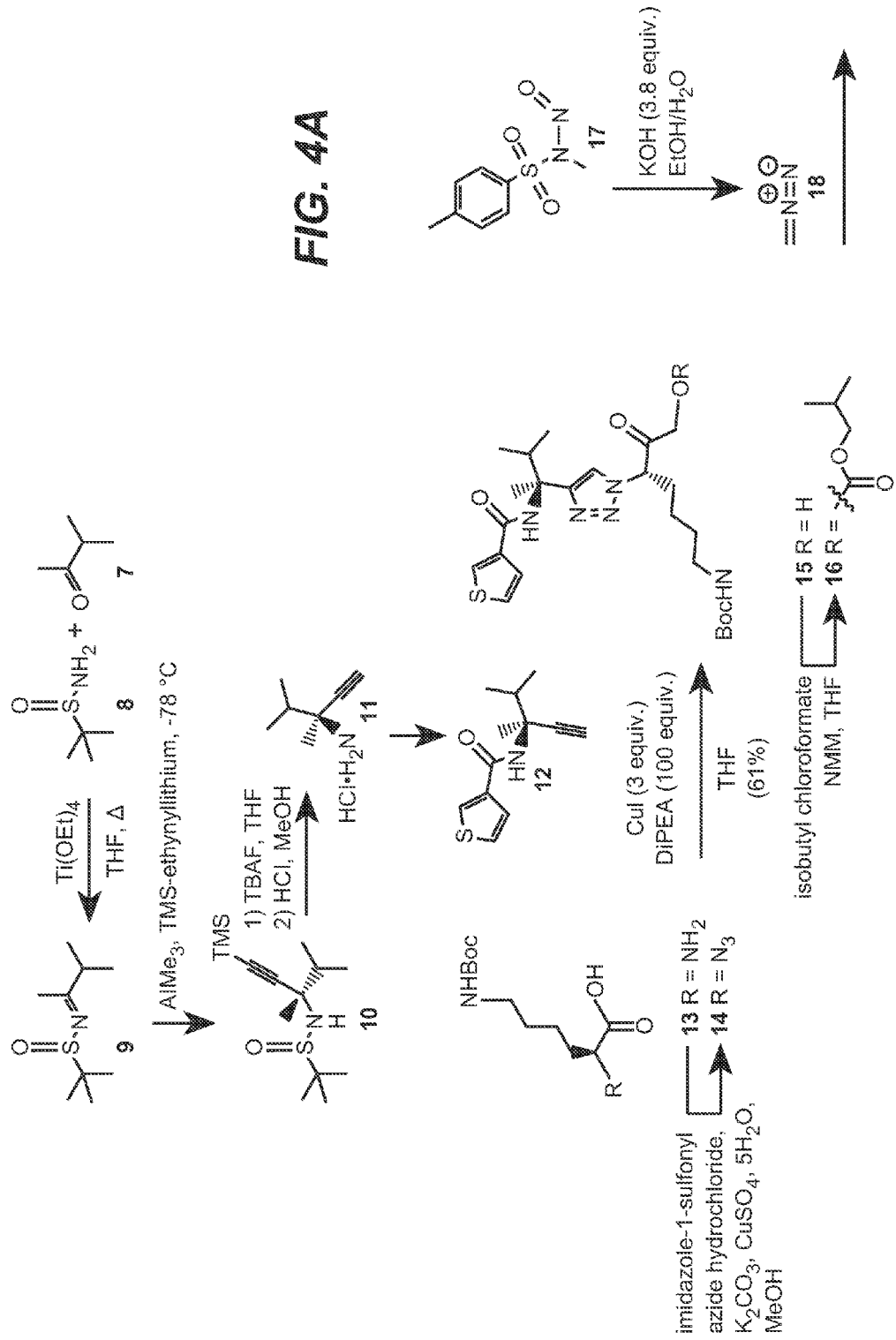
FIGS. 4A, 4B, 4C, 4D, and 4E shows the synthetic scheme used for the fluorescent imaging probe BMV011 (1) and the quenched fluorescent imaging probes BMV083 (2) and BMV084 (3).
Figure 4B:
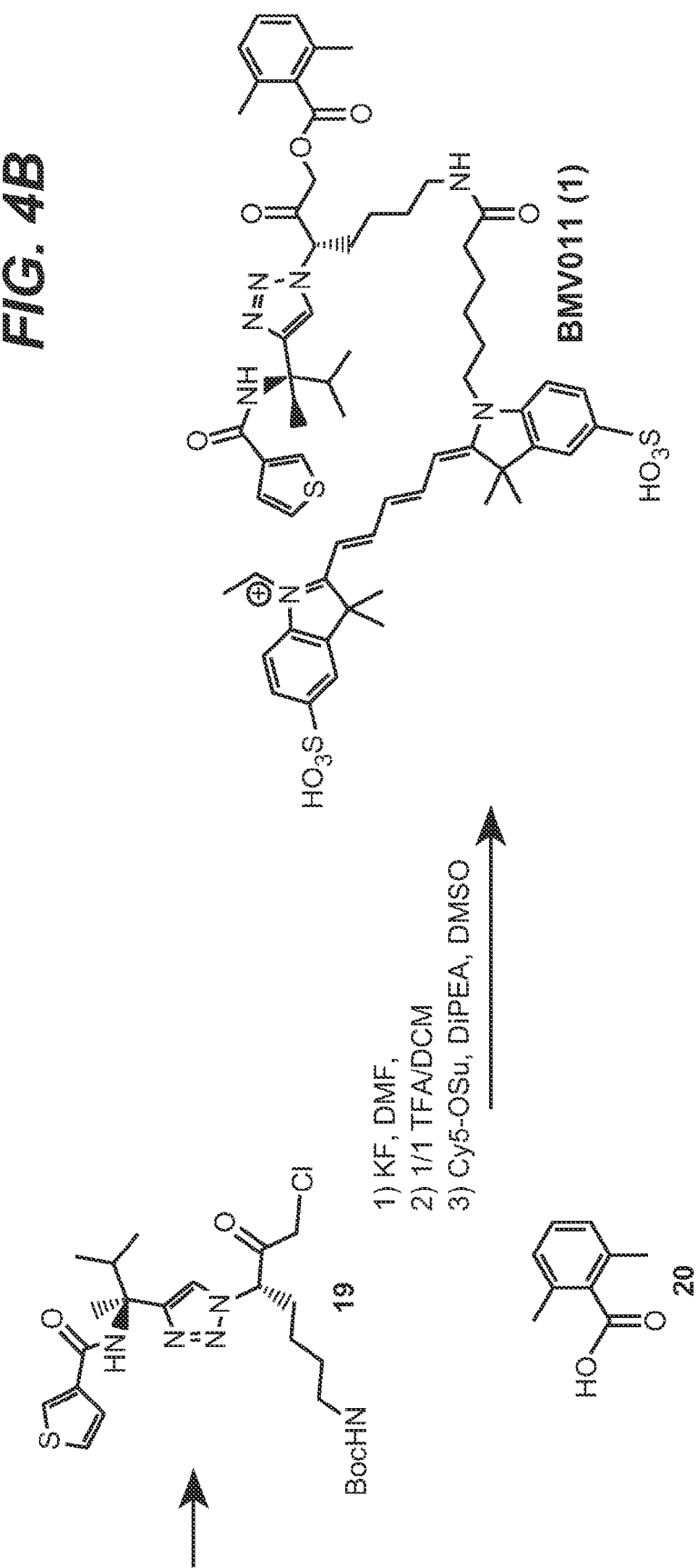
Figure 4C:
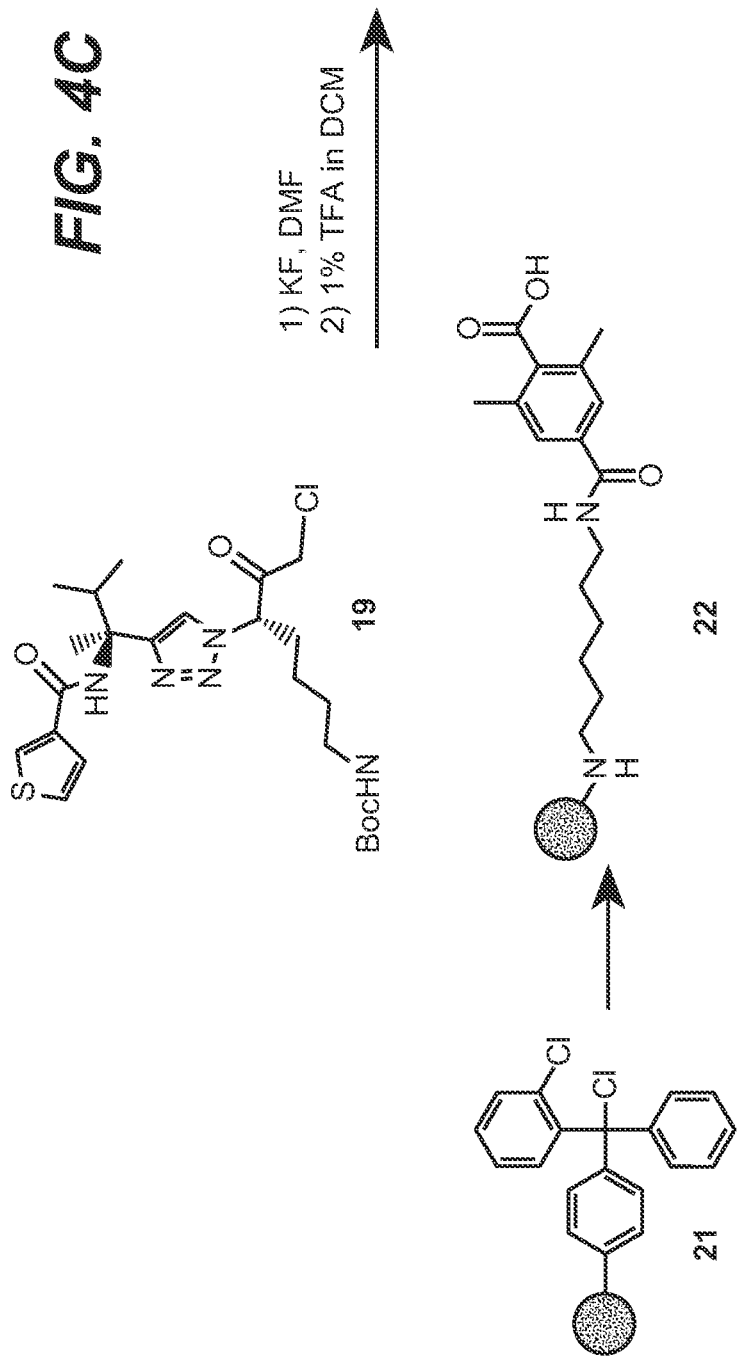
Figure 4D:
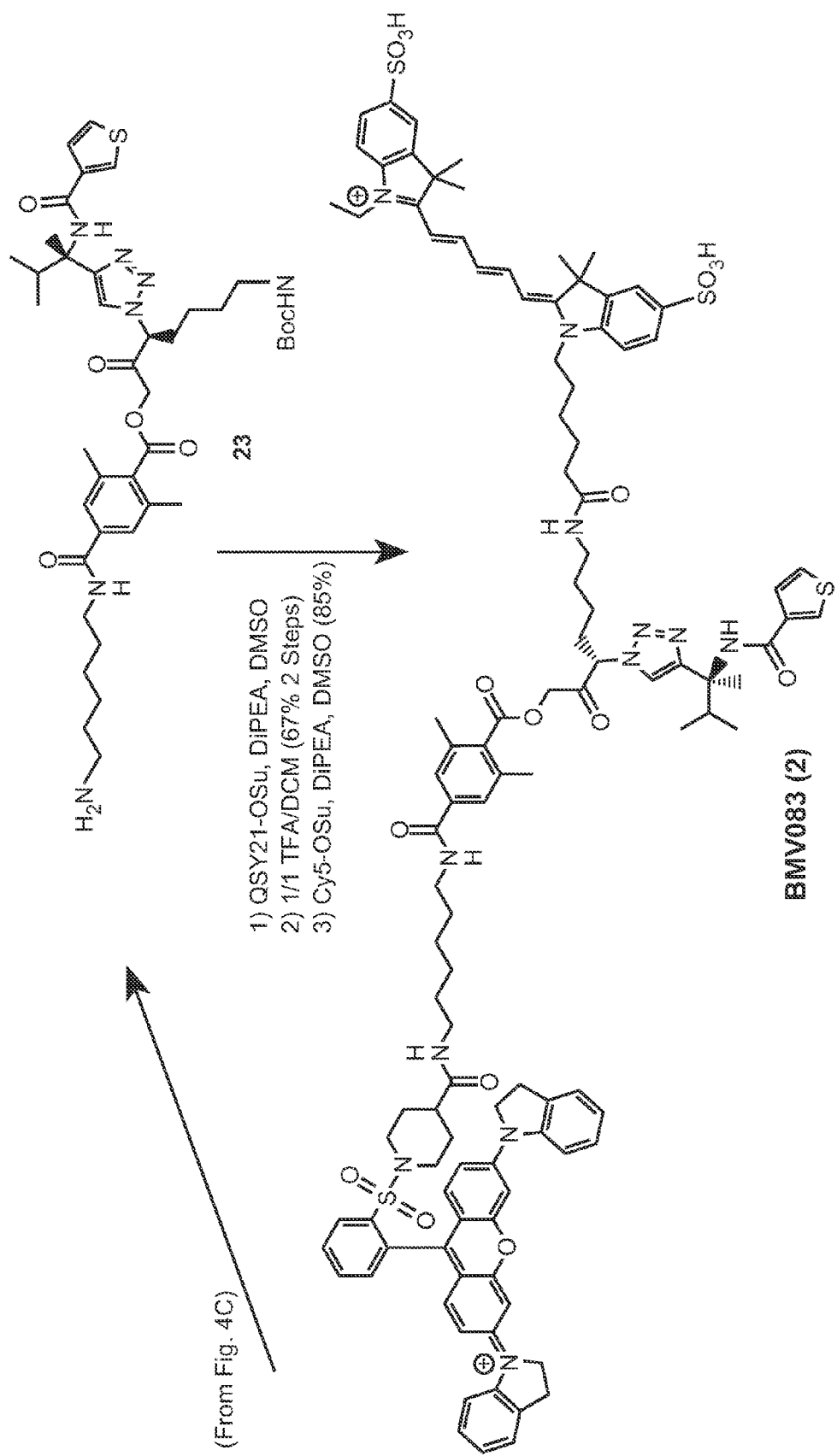
Figure 4E:
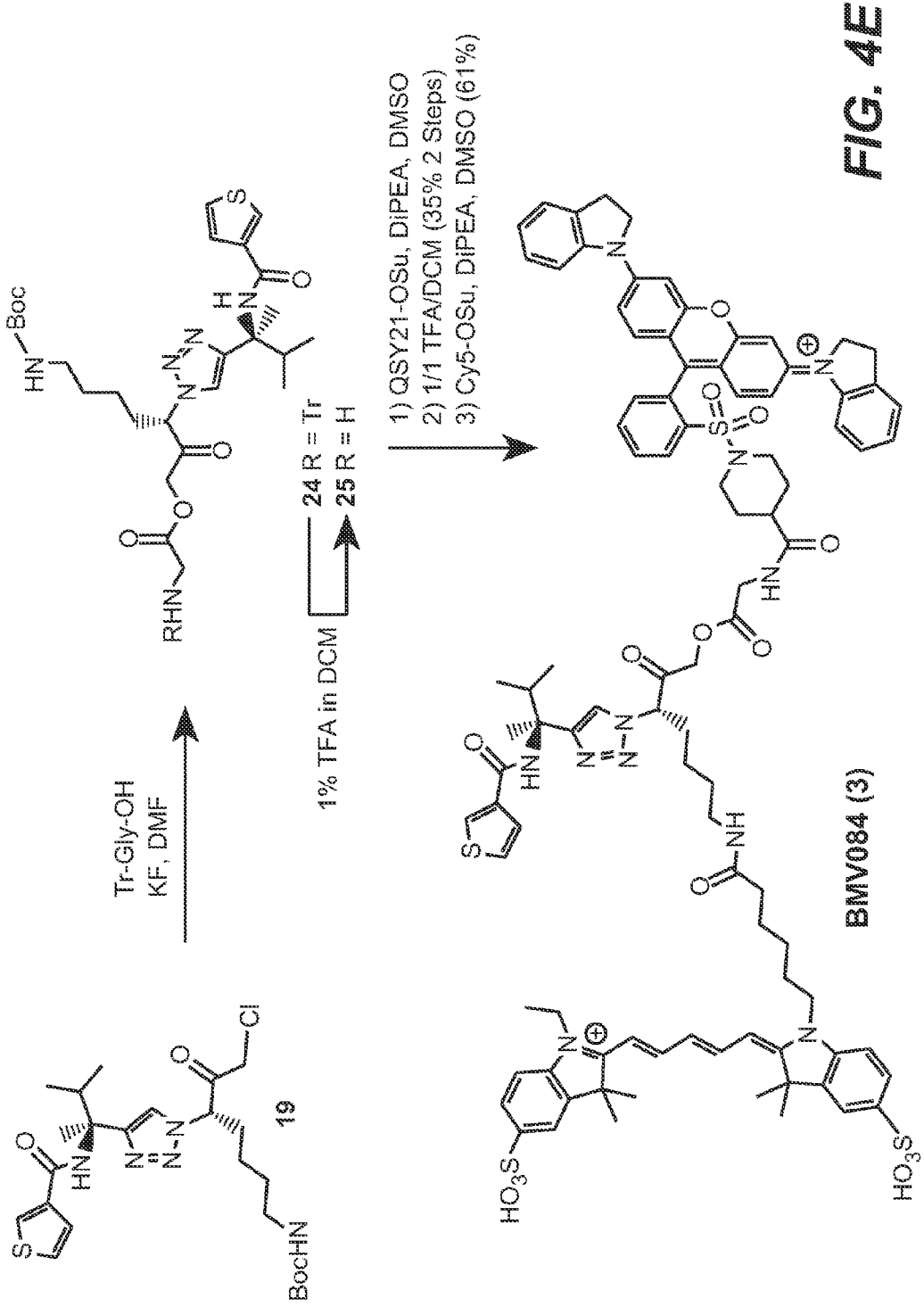
Figure 5A:
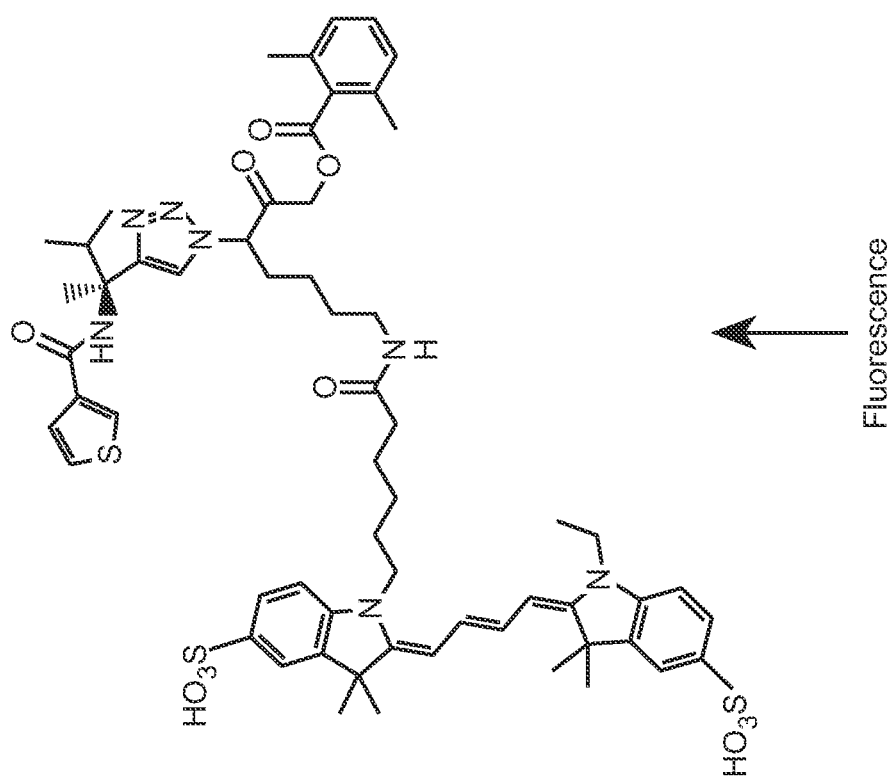
FIGS. 5A and 5B is a schematic presentation of the novel fluorescent imaging probes BMV011 (compound 1) and BMV083 (compound 2), showing the important elements of the probes; the warhead (acyloxymethyl ketone), the non-peptidic recognition element (gray elongated oval), the fluorophore (light bulb on the left side) and the quencher (⊘).
Figure 5B:
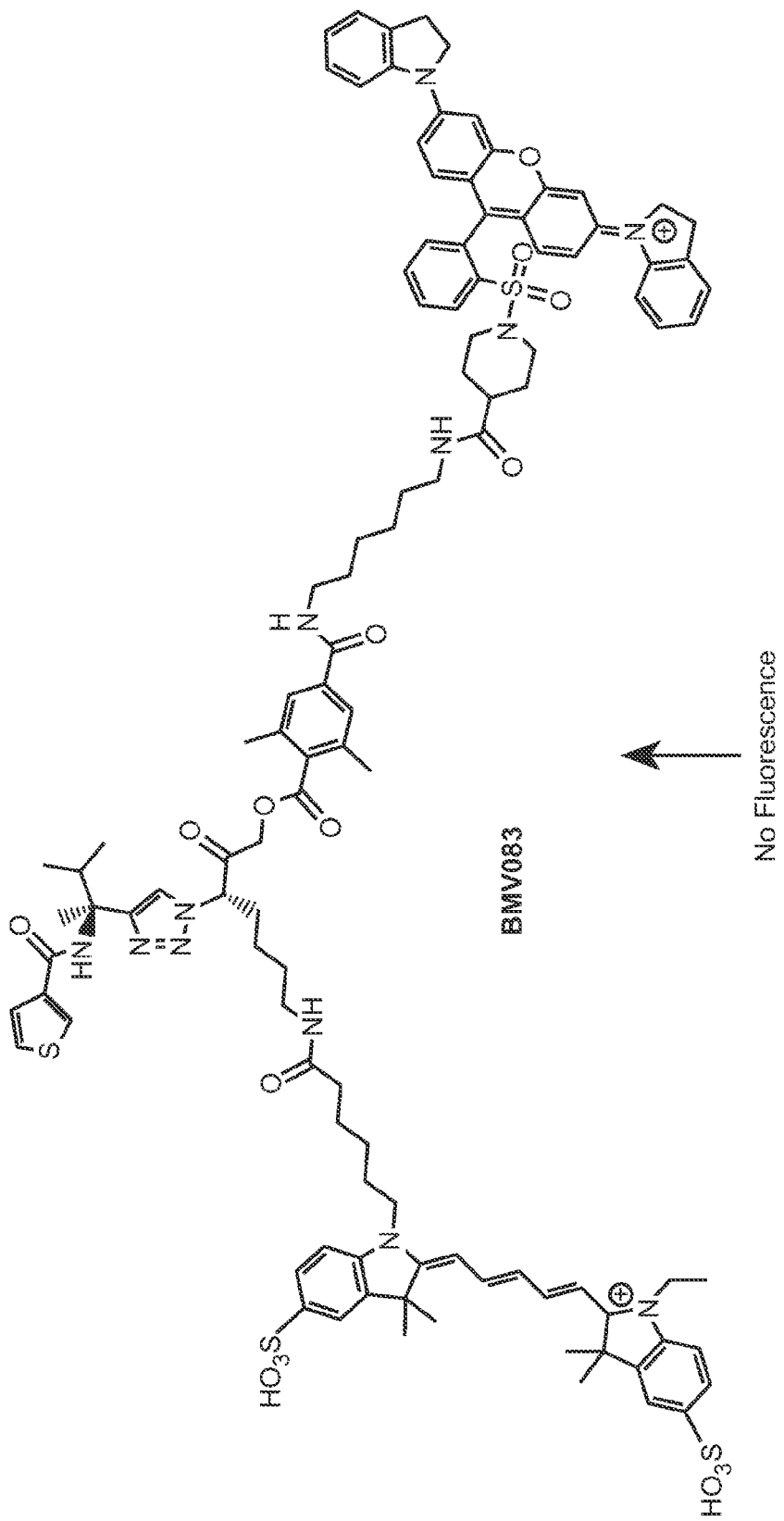

At this stage of the synthesis the free amine can be capped with the different carboxylic acids using standard peptide coupling conditions, which results in the differentially N-terminally modified fluorescent imaging probes depicted in FIG. 3. A diazotransfer reaction on commercially available ε-Boc-lysine (13) using imidazole-1-sulfonyl azide hydrochloride, (See Goddard-Borger, E. D.; Stick, R. V. An Efficient, Inexpensive, and Shelf-Stable Diazotransfer Reagent: Imidazole-1-sulfonyl Azide Hydrochloride. *Org. Len.* 2007, 9, 3797-3800) catalysed by 1 mol % $CuSO_4$ pentahydrate with 2.7 equivalents of potassium carbonate as a base resulted in α-azido-ε-Boc-lysine (14). Copper catalyzed Huisgen cycloaddition of azide 14 with alkyn 12 results in triazole 15. Chloromethylketone 19 was synthesized by activation of carboxylic acid 15 with isobutyl chloroformate and subsequent in situ reaction of 16 with diazomethane (18), followed by workup with HCl in acetic acid. A three step reaction sequence, comprised of nucleophilic displacement of the chloride with 2,6-dimethyl benzoate, acidic removal of the Boc protective group and acylation with Cy5 succinimidyl ester leads to the novel fluorescent imaging probe BMV011 (1).

Synthesis of the Probe BMV083 (2).

Mono Fmoc-protected 1,6-diaminohexane was loaded onto 2-chlorotrityl chloride resin. Fmoc deprotection, followed by coupling of the resulting free amine with 2,6-dimethyl-terephthalic acid leads to the least hindered amide 22. Reaction of the resin bound potassium carboxylate of 22 with intermediate 19 and subsequent mild acidic cleavage from the resin gains acyloxymethyl ketone 23. After capping of the free amine with the succinimidyl ester, of the quencher QSY21, deprotection Of the Boc protected amine and final introduction of the fluorophore Cy5 leads to the novel non-peptidic quenched fluorescent imaging probe BMV083 (2).

Synthesis of the Probe BMV084 (3).

Trityl protected acyloxymethyl ketone intermediate 24 was synthesized by reaction of N-trityl glycinate with chloromethyl ketone 19. Mild acidic cleavage liberated the free amine, which was capped with QSY21 succinimidyl ester. Acidic deprotection of the Boc protected amine followed by acylation with Cy5 succinimiyl ester gave the novel non-peptidic quenched fluorescent imaging probe BMV083 (3).

The synthetic scheme and exemplary compounds can be readily adapted to create a series of probes, according to the general formulas below. They are based on scaffolds attached to an AOMK group through an ester bond. On the other side of the ester bond is a quencher. When the probe covalently binds to the target protease, the quencher is released as the ester bond is hydrolyzed.

Compounds exemplified by the invention include:

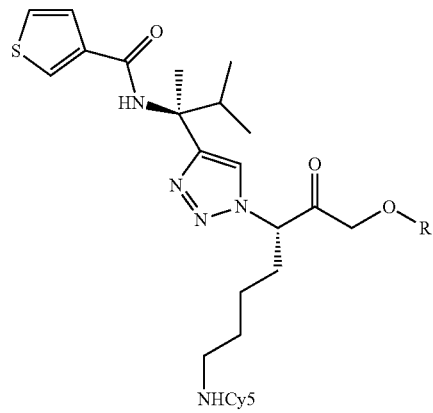

Wherein R may be:

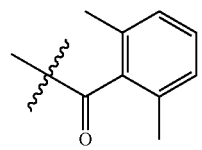 [SMILES: *C(=O)c1c(C)cccc1C]

R may include the quencher as in:

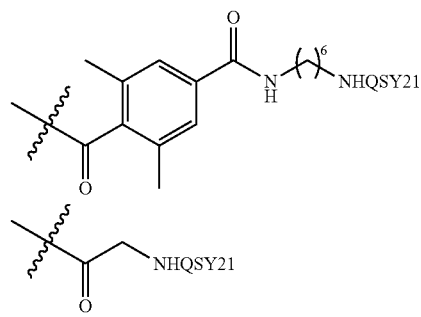

Examples of some compounds:

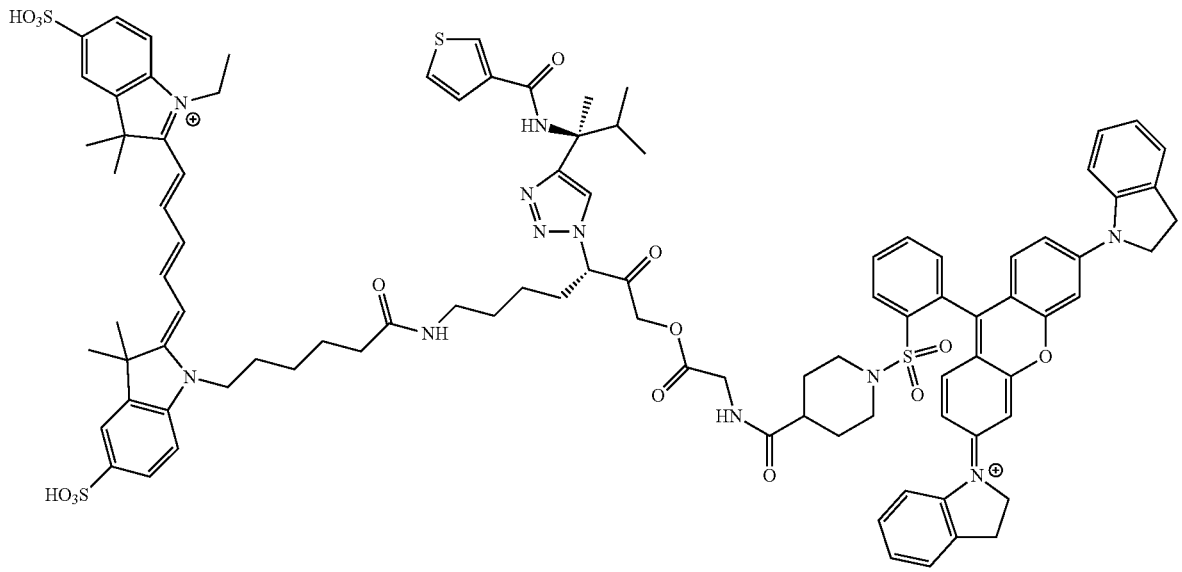

BMV084

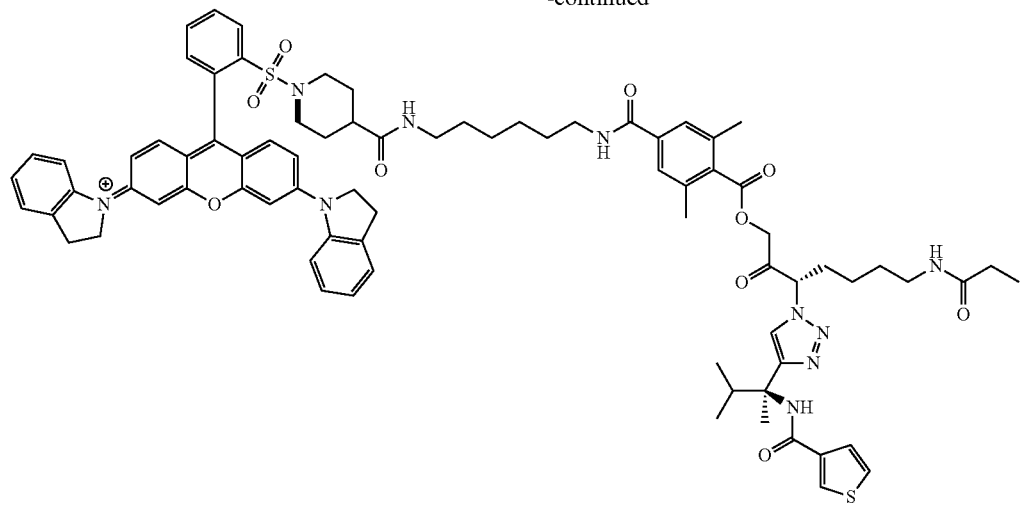

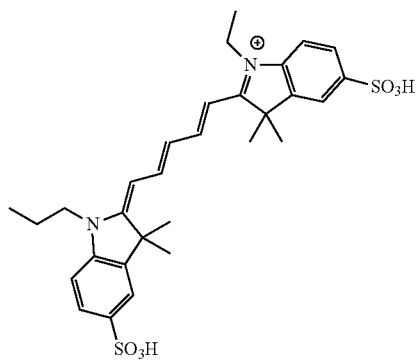

BMV083

In the above exemplary compounds the fluorophore is Cy 5 for fluorescence in the near IR region. The quencher is QSY 21.

Additional Syntheses

General

All resins and reagents were purchased from commercial suppliers and used without further purifications: All solvents used were HPLC grade. All water-sensitive reactions were preformed in anhydrous solvents under positive pressure of argon. Reactions were analyzed by LC-MS using an API 150EX single-quadrupole mass spectrometer (Applied Biosystems). Reverse-phase HPLC was conducted with an ÅKTA explorer 100 (Amersham Pharmacia Biotech) using C18 columns. NMR spectra were recorded on a Varian 400 MHz (400/100) or a Varian Inova 600 MHz (600/125 MHz) equipped with a pulsed field gradient accessory. Chemical shifts are given in ppm (δ) relative to tetramethylsilane as an internal standard. Coupling constants are given in Hz.

ABP Synthesis

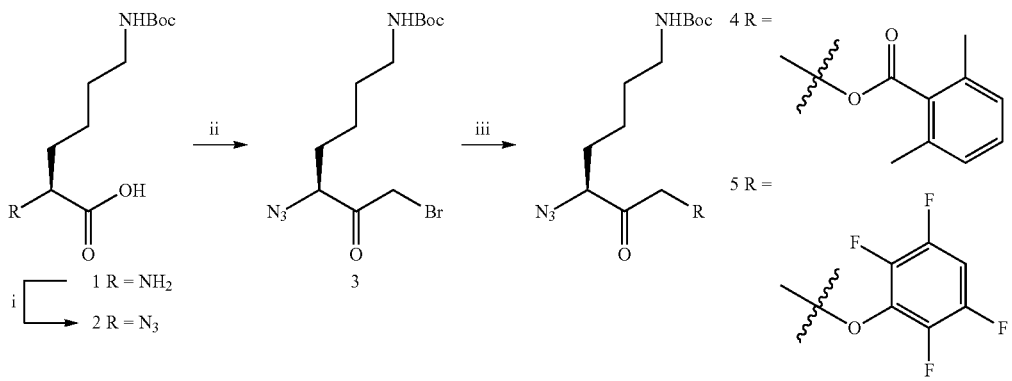

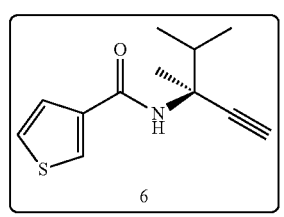

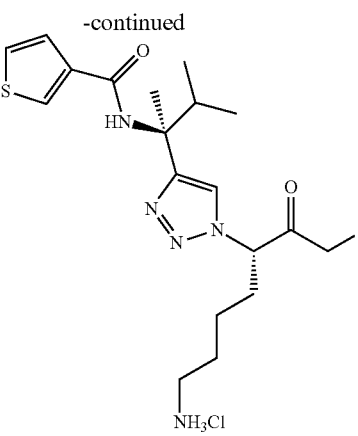

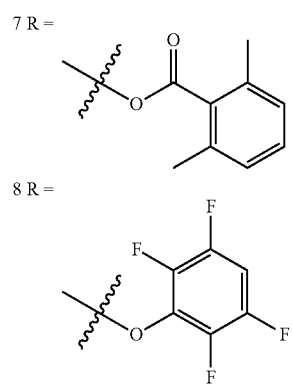

Reagents and conditions: i) Literature procedure. ii) (a) isobutylchloroformate, N-methylmorpholine, THF, -78° C. (b) CH$_2$N$_2$, THF, 0° C. (c) HBr, THF, 0° C. iii) R—OH, KF, DMF 0°C. iv. Na ascorbate, CuSO$_4$·5H$_2$O,H2O:t-BuOH (1:1), rt. v. 4M HCl/Dioxane.

Bromomethyl ketone 3.

The following method was adapted from a previous literature procedure. Azido acid 2 was prepared from Lys-(Boc)-OH according to a previously reported literature procedure. To a 0.1M solution of azido acid (3.38 g, 12.4 mmol) and N-methylmorpholine (1.34 mL, 12.4 mmol) in THF (124 mL) at -78° C. was added isobutylchloroformate (1.58 mL, 12.4 mmol). The reaction mixture was stirred for 15 min and the resulting heterogenous mixture was canula filtered into a flask at -78° C. Diazomethane, prepared from Diazald (7.25 g, 34.3 mmol), was bubbled slowly through the reaction mixture while maintaining the temperature at -78° C. After the addition of diazomethane was complete, the reaction flask was stoppered and kept in the refrigerator at -4° C. overnight. The reaction mixture was then treated with 40% aqueous HBr (1.03 mL) and stirred for 15 min at 0° C. The reaction mixture was diluted with EtOAc (150 mL) and washed with 10 wt % aqueous citric acid (2×50 mL), saturated aqueous NaHCO$_3$ (2×50 mL), and aqueous saturated NaCl (50 mL). The organic layer was dried with Na$_2$SO$_4$, filtered, and concentrated under reduced pressure to afford 3 as a yellow oil (3.8 g). The crude material was used for the subsequent reactions.

General Procedure A: α-Azido methyl ketones 4 and 5

A solution of carboxylic acid or phenol (0.57 M, 1.2-3.2 equiv) and potassium fluoride (1.2-3.0 equiv) in DMF was added to a flame-dried reaction vessel under nitrogen. The reaction mixture was cooled to 0° C. in an ice-water bath and 3 (1 equiv) was added dropwise. After stirring at 0° C. for 1.5 h, the mixture was diluted with diethyl ether (125 mL) and transferred to a separatory funnel. The organic layer was washed with aqueous sodium bicarbonate (75 mL×2) and brine (75 mL). The organic layer was dried over anhydrous sodium sulfate, filtered, and concentrated under reduced pressure. The product was purified by flash chromatography (7:3 hexanes:EtOAc) to afford the pure product. α-Azido methyl ketone 4. Procedure A was followed using 2,6-dimethyl benzoic acid (0.82 g, 0.57 M, 5.48 mmol, 1.2 equiv), potassium fluoride (3.16 g, 5.48 mmol, 1.2 equiv), and (S)-tert-butyl (5-azido-7-bromo-6-oxoheptyl)carbamate 4 (1.60 g, 4.59 mmol, 1 equiv). After chromatography the product was obtained as a pale yellow oil (0.62 g, 33%). α-Azido methyl ketone 5. Procedure A was followed using 2,3,4,6-tetrafluorophenol (2.43 g, 0.57 M, 14.7 mmol, 3.2 equiv) and potassium fluoride (8.47 g, 14.7 mmol, 3.2 equiv), and (S)-tert-butyl (5-azido-7-bromo-6-oxoheptyl)carbamate 5 (1.60 g, 4.59 mmol, 1 equiv). After chromatography the product was obtained as a pale yellow oil (0.77 g, 39%).

General Procedure B: Copper(I)-catalyzed 1,2,3-triazole formation

The procedure for the synthesis was adapted from a previous literature report.[3] (S)—N-(3,4-dimethylpent-1-yn-3-yl)thiophene-2-carboxamide (6) was prepared according to a previously reported literature procedure.[4] To a 0.25 M 1:1 H$_2$O/t-BuOH solution of azido-methyl ketone 4 and 5 (1.0 equiv) and (S)—N-(3,4-dimethylpent-1-yn-3-yl)thiophene-2-carboxamide (6) (1.0 equiv), was added a freshly prepared 1.0 M aqueous solution of sodium ascorbate (1.0 equiv). A freshly prepared 0.3 M aqueous solution of copper(II) sulfate pentahydrate (0.1 equiv) was added to the reaction mixture, which was vigorously stirred overnight. The reaction mixture was diluted with 10 mL of water and then extracted with CH$_2$Cl$_2$ (3×10 mL). The organic layer was washed with brine (15 mL), dried over sodium sulfate, filtered, and concentrated under reduced pressure. The crude product was purified by flash chromatography (7:3 hexanes:EtOAc) to afford the desired product as a ~1:1 mixture of epimers at the stereocenter alpha to the ketone. Synthesis of 7. General Procedure B was followed using azido-aryloxy methyl ketone 4 (0.091 g, 0.22 mmol), (S)—N-(3,4-dimethylpent-1-yn-3-yl)thiophene-2-carboxamide (6) (0.050 g, 0.22 mmol) in 0.99 mL of 1:1 H$_2$O/t-BuOH, 1.0 M aqueous solution of sodium ascorbate (0.22 mL, 0.218 mmol), and 0.3 M aqueous solution of copper(II) sulfate pentahydrate (0.07 mL, 0.0218 mmol). Purification by flash chromatography afforded the Boc-protected intermediate in 57% yield, which was (0.079 g, 0.124 mmol) was directly treated with HCl as a 4.0 M solution in 1,4-dioxane (0.31 mL, 1.24 mmol). The solution was stirred at rt for 2 h and was then concentrated to afford the crude product, which was purified by HPLC [preparatory reverse phase $C_{18}$ column (24.1×250 mm), $CH_3CN/H_2O$ 0.1% TFA, 5:95 to 95:5 over 55 min; 10 mL/min, 254 nm detection]. Fractions were combined and the $CH_3CN$ was evaporated. The resulting aqueous solution was extracted with $CH_2Cl_2$, dried with $Na_2SO_4$, filtered, and concentrated to yield the HCl salt 7 in 85% yield (0.06 g). MS (ESI): m/z calcd for $C_{28}H_{37}N_5O_4S+H^+$ 540.3 [M+1-1]$^+$. found 540.0. Synthesis of 8. General Procedure B was followed using azido-aryloxy methyl ketone 5 (0.070 g, 0.25 mmol), (S)—N-(3,4-dimethylpent-1-yn-3-yl)thiophene-2-carboxamide (6) (0.06 g, 0.25 mmol) in 1.00 mL of 1:1 $H_2O$/t-BuOH, 1.0 M aqueous solution of sodium ascorbate (0.25 mL, 0.25 mmol), and 0.3 M aqueous solution of copper(II) sulfate pentahydrate (0.08 mL, 0.025 mmol). Purification by flash chromatography afforded the Boc-protected intermediate in 56% yield (93 mg), which was directly treated with HCl as a 4.0 M solution in 1,4-dioxane (0.33 mL, 1.3 mmol). The solution was stirred at rt for 2 h and was then concentrated to afford the crude product, which was purified by HPLC [preparatory reverse phase $C_{18}$ column (24.1×250 mm), $CH_3CN/H_2O$ 0.1% TFA, 5:95 to 95:5 over 55 min; 10 mL/min, 254 nm detection]. Fractions were combined and the $CH_3CN$ was evaporated. The resulting aqueous solution was extracted with $CH_2Cl_2$, dried with $Na_2SO_4$, filtered, and concentrated to yield the HCl salt 8 in 74% yield (0.057 g). MS (ESI): m/z calcd for $C_{25}H_{29}F_4N_5O_3S+H^+$ 556.2 [M+H]$^+$. found 555.9.

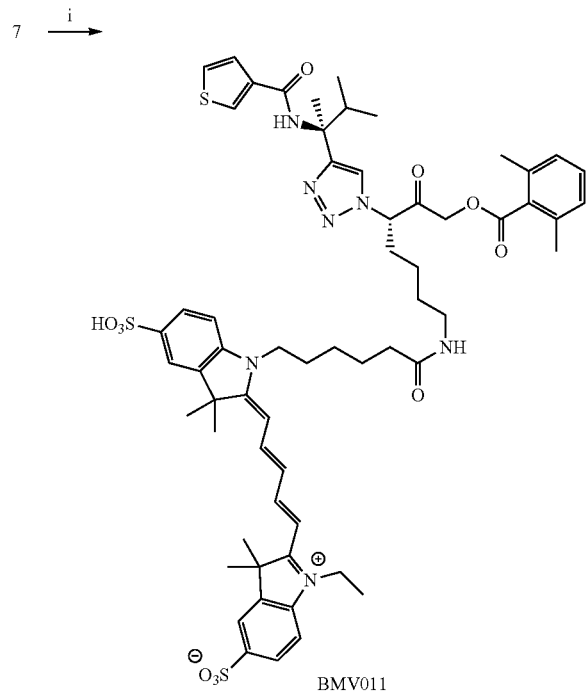

BMV011

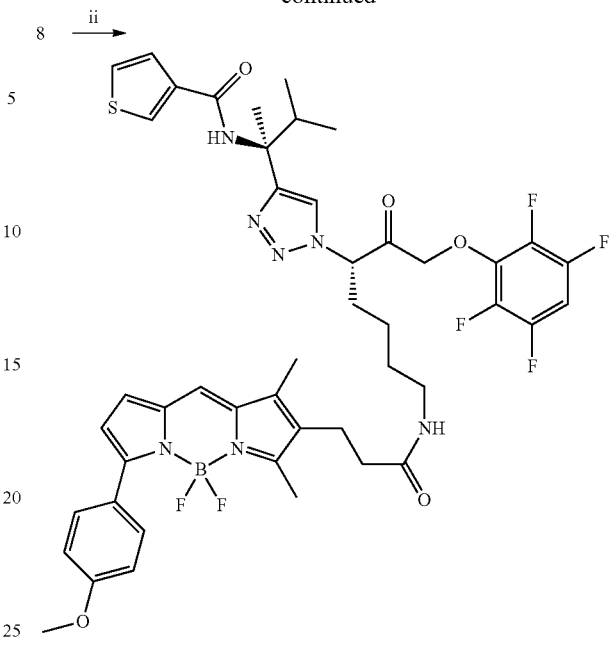

BMV099

Reagents and conditions: i) Cy5-OSu, DiPEA, DMSO. ii) BODIPY TMR—STP, DiPEA, DMSO.

BMV011.

To a solution of 7 (2.5 mg, 4.3 μmol) and Cy5-succinimidyl ester (4.6 mg, 5.8 μmol, 1.2 equiv.) in DMSO DiPEA (3.74 μl, 21.5 μmol, 5 equiv.) was added and the reaction mixture was stirred for 2 hr. HPLC purification (preparatory reverse phase $C_{18}$ column, $CH_3CN/H_2O$ 0.1% TFA, 20:80 to 55:45 over 30 min; 5 mL/min), followed by lyophilization afforded BMV011 as a blue powder (3.6 mg, 3.1 μmol, 71%). H NMR (400 MHz, MeOD) δ=8.31 (t, J=13.1, 2 H), 8.15-8.01 (m, 2H), 7.93-7.83 (m, 4H), 7.49-7.38 (m, 2H), 7.31 (m, 2H), 7.23-7.17 (m, 1H), 7.06-7.02 (m, 2H), 6.70-6.59 (m, 1H), 6.39-6.29 (m, 2H), 5.63 (dd, J=9.7, 3.7, 1H), 5.12 (dd, J=17.2, 5.6, 1 H), 4.99 (dd, J=17.3, 4.8, 1H), 4.20-4.04 (m, 4H), 3.19-2.98 (m, 3H), 2.69-2.55 (m, 2H), 2.37-2.25 (m, 6H), 2.14 (m, 3H), 1.82 (s, 3H), 1.79-1.70 (m, 8H), 1.66 (dd, J=14.4, 7.1, 2H), 1.54-1.26 (m, 8H), 1.18 (m, 2H), 1.04-0.77 (m, 6H). MS (ESI): m/z calcd for $C_{61}H_{76}N_7O_{11}$ $S_3^+$1178.5 [M$^+$]. found 1178.6.

BMV099.

To a solution of 8 (0.97 mg, 1.64 μmol) and BODIPY TMR-4-sulfotetrafluorophenyl (1.07 mg, 1.64 μmol, 1 equiv.) in DMSO DiPEA (1.43 μl, 8.2 μmol, 5 equiv.) was added and the reaction mixture was stirred for 2 hr. HPLC purification (preparatory reverse phase C18 column, $CH_3CN/H_2O$ 0.1% TFA, 40:60 to 75:25 over 30 min; 5 mL/min), followed by lyophilization afforded BMV099 as a dark red powder (0.81 mg, 0.87 μmol, 53%). $^1$H NMR (400 MHz, MeOD) δ=8.06-7.99 (m, J=2.1, 1 H), 7.95-7.79 (m, 3H), 7.49-7.36 (m, 2H), 7.11-7.03 (m, 1H), 7.01-6.90 (m, 2H), 6.89-6.78 (m, 1H), 6.58 (d, J=3.3, 1 H), 6.07 (d, J=6.6, 1 H), 5.53-5.40 (m, 1H), 4.78-4.65 (m, 21-1), 3.84 (s, 3H), 2.81-2.69 (m, 2H), 2.64-2.55 (m, 2H), 2.47 (s, 3H), 2.42-2.37 (m, 1H), 2.34-2.27 (m, 2H), 2.24 (s, 3H), 2.01-1.91 (m, 2H), 1.77 (s, 3H), 1.49-1.20 (m, 4H), 0.95-0.79 (m, 6H). MS (ESI): m/z calcd for $C_{46}H_{48}BF_6N_7O_5S+H^+$ 936.4 [M+H]$^+$. found 936.6.

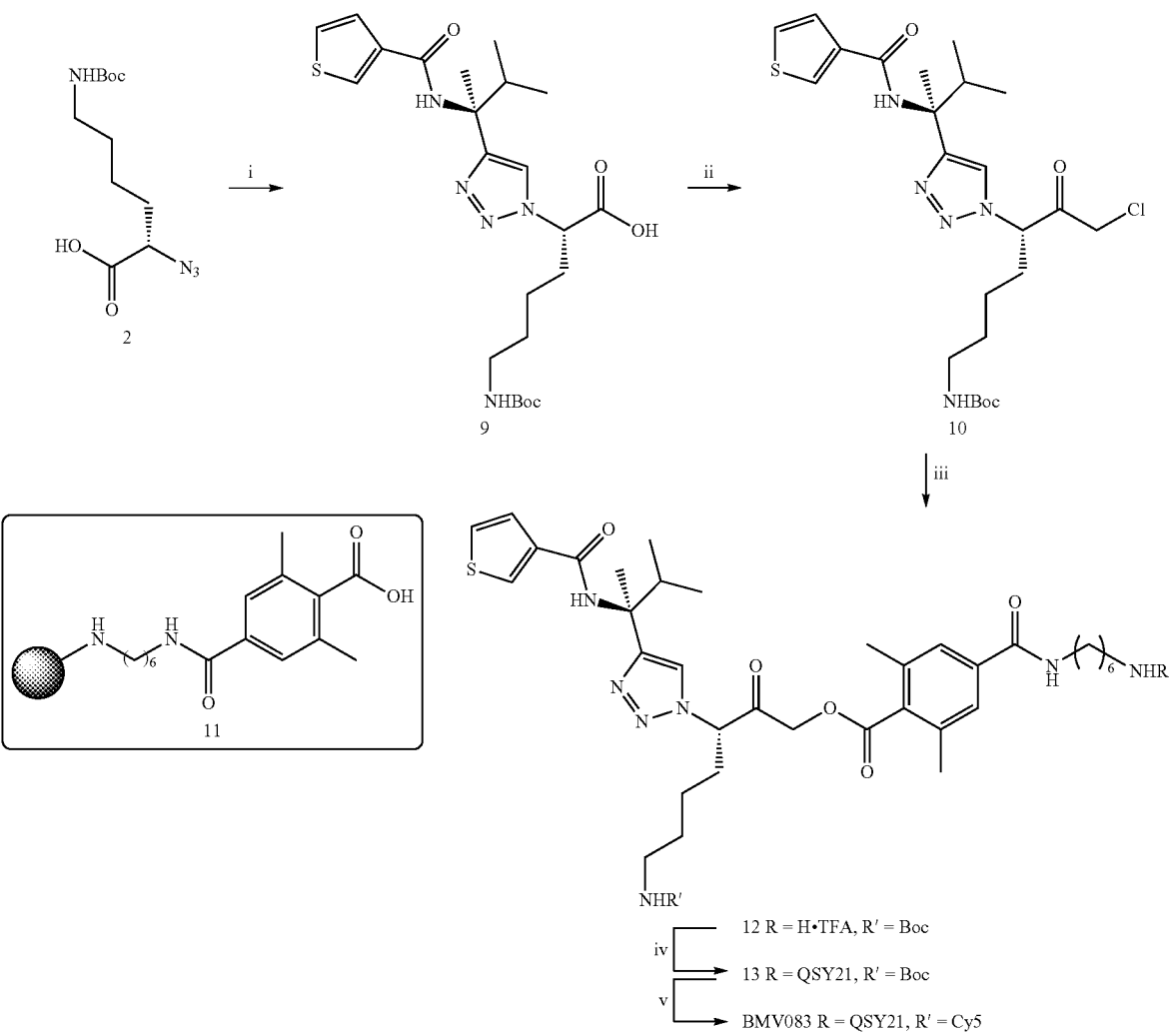

Reagents and conditions: i) 6, CuI, DiPEA, THF. ii) (a) isobutylchloroformate, N-methylmorpholine, THF, -60° C. (b) CH$_2$N$_2$, THF, -60° C. (c) HCl, glacial acetic acid, -60° C. iii) (a) 7, KF, DMF. (b) 1% TFA in DCM. iv) QSY21-OSu, DiPEA, DMSO. v) (a) 50% TFA in DCM. (b) Cy5-OSu, DiPEA, DMSO.

(S)-6-((tert-butoxycarbonyl)amino)-2-(4-((S)-3-methyl-2-(thiophene-3-carboxamido)butan-2-yl)-1H-1,2,3-triazol-1-yl)hexanoic acid (9). To a stirred solution of alkyne (40 mg, 0.18 mmol) and N$_3$-Lys(Boc)-OH (49.3 mg, 0.18 mmol, 1 equiv) in THF was added DiPEA (3.14 ml, 18 mmol, 100 equiv) and copper iodide (0.1 g, 0.54 mmol, 3 equiv). After 24 hr ethyl acetate was added and the organic layer was washed with 1M HCl and separated. The organic layer was dried over MgSO$_4$ and concentrated in vacuo. HPLC purification (preparatory reverse phase C18 column, CH$_3$CN/H$_2$O 0.1% TFA, 15:85 to 50:50 over 30 min; 5 mL/min), followed by lyophilization afforded the title compound as a white powder (54.1 mg, 109.7 µmol, 61%). $^1$H NMR (400 MHz, CDCl$_3$+MeOD) δ ppm 8.03 (dd, J=1.4 Hz, J=3.0 Hz, 1H), 7.94 (s, 1H), 7.46 (dd, J=1.2 Hz, J=5.2 Hz, 1H), 7.33 (dd, J=2.8 Hz, J=5.2 Hz, 1H), 5.34 (dd, J=5.2 Hz, J=10.0 Hz, 1H), 3.04 (t, J=7.0 Hz, 2H), 2.79 (m, 1H), 2.32 (m, 1H), 2.19 (m, 1H), 1.86 (s, 3H), 1.48 (m, 2H), 1.42 (s, 9H), 1.35 (m, 1H), 1.24 (m, 1H), 1.01 (d, J=6.8 Hz, 3H), 0.80 (d, J=6.8 Hz, 3H). $^{13}$C NMR (101 MHz, CDCl$_3$+MeOD) δ ppm 170.8, 163.4, 150.9, 137.8, 129.1, 126.7, 126.4, 122.5, 94.7, 63.6, 58.2, 35.6, 32.1, 29.2, 28.6, 23.2, 17.7, 17.3. MS (ESI): m/z calcd for C$_{23}$H$_{35}$N$_5$O$_5$S+H$^+$ 494.2 [M+H]$^+$. found 494.3.

tert-butyl ((S)-7-chloro-5-(4-((S)-3-methyl-2-(thiophene-3-carboxamido)butan-2-yl)-1H-1,2,3-triazol-1-yl)-6-oxo-heptyl)carbamate (10). To a stirred solution of carboxylic acid 9 (50 mg, 100.9 µmol) in 5 ml dry THF under argon atmosphere at -60° C. was added N-methylmorpholine (14 µl, 126.3 µmol, 1.25 equiv.) and isobutyl chloroformate (14.9 µl, 116.7 µmol, 1.15 equiv.). After 30 min an etheral solution of diazomethane (0.95 ml 0.6 M, 0.57 mmol, 5.6 equiv.) was added to above solution at -60° C. and the reaction mixture was stirred for 1 hr. A 1:1 solution of conc. HCl and glacial acetic acid was added dropwise to the reaction mixture, before ethyl acetate and water were added. The organic layer was washed with brine, sat. aq. NaHCO$_3$ and dried over MgSO$_4$. Concentration in vacuo afforded the crude title compound, which was used without purification. $^1$H NMR (400 MHz, CDCl$_3$+MeOD) δ ppm 7.89 (dd, J=1.5 Hz, J=3.0 Hz, 1H), 7.71 (s, 1H), 7.39 (dd, J=1.2 Hz, J=5.2 Hz, 1H), 7.36 (dd, J=2.9 Hz, J=5.2 Hz, 1H), 7.06 (s, 1H), 5.59 (dd, J=4.6 Hz, J=10.0 Hz, 1H), 4.80 (s, 1H), 4.17 (s, 2H), 3.06 (m, 2H), 2.83 (m, 2H), 2.30 (m, 1H), 2.11 (m, 1H), 1.88 (s, 3H), 1.48 (m, 2H), 1.42 (s, 9H), 1.34 (m, 1H), 1.22 (m, 1H), 0.99 (d, J=6.8 Hz, 3H), 0.80 (d, J=6.8 Hz, 3H). MS (ESI): m/z calcd for C$_{24}$H$_{36}$ClN$_5$O$_4$S+H$^+$ 526.2 [M+H]$^+$. found 526.3.

Intermediate 13.

Chloromethyl ketone 10 (21 mg, 40 µmol, 1 equiv.) and KF (23 mg, 0.4 mmol, 10 equiv.) were added to resin 11[5] in DMF. After shaking for 2 hr, the resin was washed with DMF (3×) and DCM (3×), before being treated with 1% TFA in DCM for 20 min (3×). The combined fractions were coevaporated with toluene and the crude was HPLC purified (preparatory reverse phase C18 column, $CH_3CN/H_2O$ 0.1% TFA, 10:90 to 45:55 over 30 min; 5 ml/min), followed by lyophilization to yield compound 12 as a white powder (5.5 mg, 6.14 mmol, 15%). MS (ESI): m/z calcd for $C_{40}H_{59}N_7O_7S+H^+$ 782.4 $[M+H]^+$. found 782.7. To a solution of 12 (4.0 mg, 4.46 µmol) and QSY21-succinimidyl ester (3.64 mg, 4.46 µmol, 1 equiv.) in DMSO DiPEA (3.9 µl, 22.3 µmol, 5 equiv.) was added and the reaction mixture was stirred for 2 hr. HPLC purification (preparatory reverse phase $C_{18}$ column, $CH_3CN/H_2O$ 0.1% TFA, 30:70 to 70:30 over 30 min; 5 mL/min), followed by lyophilization afforded 13 as a black powder (5.67 mg, 3.92 µmol, 88%). $^1H$ NMR (400 MHz, MeOD) δ=8.17-8.15 (m, 1H), 7.95 (m, 1H), 7.91-7.86 (m, 3H), 7.59 (d, J=8.2, 2H), 7.54-7.49 (m, 4H), 7.48-7.43 (m, 4H), 7.42-7.39 (m, 2H), 7.38 (s, 1H), 7.36 (s, 1H), 7.33 (m, 1H), 7.28 (m, 4H), 7.14 (t, J=7.4, 2H), 5.49 (dd, J=9.5, 4.4, 1H), 4.94 (m, 2H), 4.39-4.23 (m, 4H), 3.42 (d, J=12.3, 2H), 3.07 (m, 2H), 3.00 (m, 2H), 2.91 (m, 1H), 2.76-2.58 (m, 4H), 2.37 (s, 3H) 2.37-2.28 (m, 4H), 2.19 (m, 2H), 1.82 (s, 3H), 1.78 (d, J=11.0, 1H), 1.67 (m, 3H), 1.49 (m, 6H), 1.39 (s, 9H), 1.38-1.34 (m, 2H), 1.26 (m, 5H), 0.98-0.80 (m, 6H). MS (ESI): m/z calcd for $C_{81}H_{93}N_{10}O_{11}S_2^+$ 1445.6 $[M^+]$. found 1445.5.

BMV083.

Boc protected 13 (5.6 mg, 3.9 µmol) was taken up in a 1/1 mixture of DCM and TFA. After 30 min the reaction mixture was coevaporated with toluene (3×). The crude amine was dissolved in DMSO and Cy5-succinimidyl ester (3.4 mg, 4.3 µmol, 1.1 equiv.) and DiPEA (3.4 µl, 19.5 µmol, 5 equiv.) was added and the reaction mixture was stirred for 1 hr. HPLC purification (preparatory reverse phase $C_{18}$ column, $CH_3CN/H_2O$ 0.1% TFA, 40:60 to 85:15 over 35 min; 5 mL/min), followed by lyophilization afforded 13 as a black powder (6.69 mg, 3.37 µmol, 86%). $^1H$ NMR (600 MHz, $CD_3CN$) δ=8.13 (dd, J=5.9, 3.4, 1H), 8.09-8.00 (m, 3H), 7.93-7.85 (m, 4H), 7.78 (m, 2H), 7.75 (m, 2H), 7.54 (d, J=8.0, 2H), 7.43 (m, 2H), 7.39-7.34 (m, 4H), 7.33-7.31 (m, 2H), 7.25-7.17 (m, 5H), 7.07 (t, J=7.5, 2H), 6.52-6.46 (m, 1H), 6.18 (d, J=13.7, 2H), 5.54-5.47 (m, 1H), 5.07 (dd, J=17.4, 8.8, 1H), 4.96 (dd, J=17.3, 9.5, 1H), 4.19 (dd, J=15.8, 7.9, 4H), 3.97 (m, 4H), 3.26 (d, J=12.6, 2H), 3.24-3.16 (m, 6H), 3.04-2.93 (m, 6H), 2.58 (s, 2H), 2.49 (dt, J=18.1, 8.7, 4H), 2.28-2.19 (m, 6H), 2.09 (m, 2H), 2.03 (t, J=7.5, 2H), 1.72-1.65 (m, 4H), 1.61 (s, 6H), 1.57 (m, 3H), 1.50 (dt, J=15.2, 7.5, 2H), 1.44 (dt, J=14.1, 6.9, 2H), 1.35-1.13 (m, 16H), 1.11-0.97 (m, 3H), 0.88-0.71 (m, 6H). MS (ESI): m/z calcd for $C_{109}H_{124}N_{12}O_{16}S_4^{2+}$ 1985.8 $[M^{2+}]$. found 1985.5.

Example 2

Testing of Potency and Labeling by Probes

The kinetics of inhibition was determined by progress curve method under pseudo-first order conditions with at least 10-fold molar excess of inhibitor. Recorded progress curves were analyzed by non-linear regression according to the following equation (12). $[P]=v_z(1-e^{-s-1})/k$ where [P] is the product, vz is the velocity at time zero and k is the pseudo first order rate constant. Apparent rate constant (kapp) was determined from the slope of plot k versus [I]. Due to irreversible and competitive mechanism of inhibition, kapp was converted to the association constant (kass) using the equation below:

$$k_{ass}=k_{app}(1+[S]/K_M)$$

Activity of human cathepsin L was measured using the fluorogenic substrate Z-FRAMC37 (Bachem, USA) (Km=7.1 µM) and cathepsin B was assayed against the fluorogenic substrate Z-RR-AMC38 (Bachem, USA) (Km=114 µM). Concentration of substrates during the measurement was 10 µM. Cathepsins B and L (1 nM final concentrations) were incubated with inhibitor concentrations, ranging from 10 to 2000 nM, in the presence of 10 µM of appropriate substrate. Total volume during the measurement was 100 µl. Increase of fluorescence (370 nm excitation, 460 nm emission) was continuously monitored for 30 minutes by Spectramax M5 spectrofluorimeter.

(Molecular Devices, USA) and inhibition curves were recorded. DMSO concentration during all measurements was 3.5%.

Quenching efficiency between 0 and 2 micromolar concentration was measured and both BMV083 and BMV084 were completely quenched.

Example 3

Labeling Profile and Serum Stability of BMV011 and BMV 083

Figure 6A:
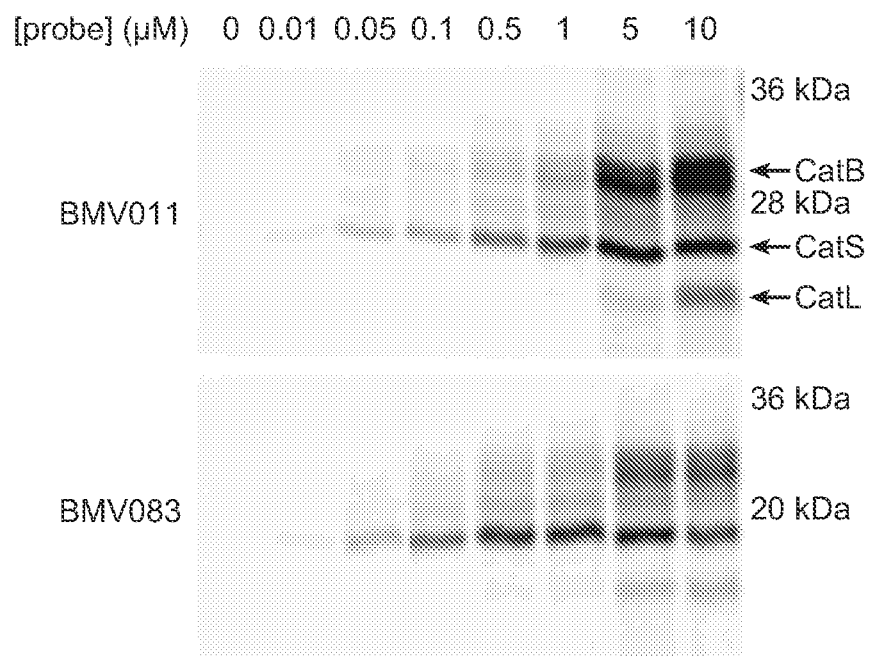
FIGS. 6A and 6B is a series of gels showing a labeling profile and serum stability of BMV011 (1) and BMV083 (2). It shows the fluorescent readout of labeled proteins (40 μg total protein) resolved on 15% SDS-PAGE. Living RAW 264.7 cells (some $2 \cdot 10^6$ cells) were exposed to (6A) the indicated concentrations of BMV011 and BMV083 or (6B) 1 μM BMV011 and BMV083 for 3 hr. at 37° C., before being harvested and lysed. Where indicated, the probes were exposed to mouse serum (1:9 DMSO stock:serum) for 1 or 4 hr or the cells were pre-incubated with 50 μM JPM (Inh.) for 2 hr. at 37° C. Concentration dependent labeling of cathepsin B, S and L is observed. At lower concentrations, cathepsin S is the predominantly labeled protease. BMV011 and BMV083 are stable in serum, proven by the ability to label the cathepsins with equal intensity after prolonged exposure to serum.
Figure 6B:
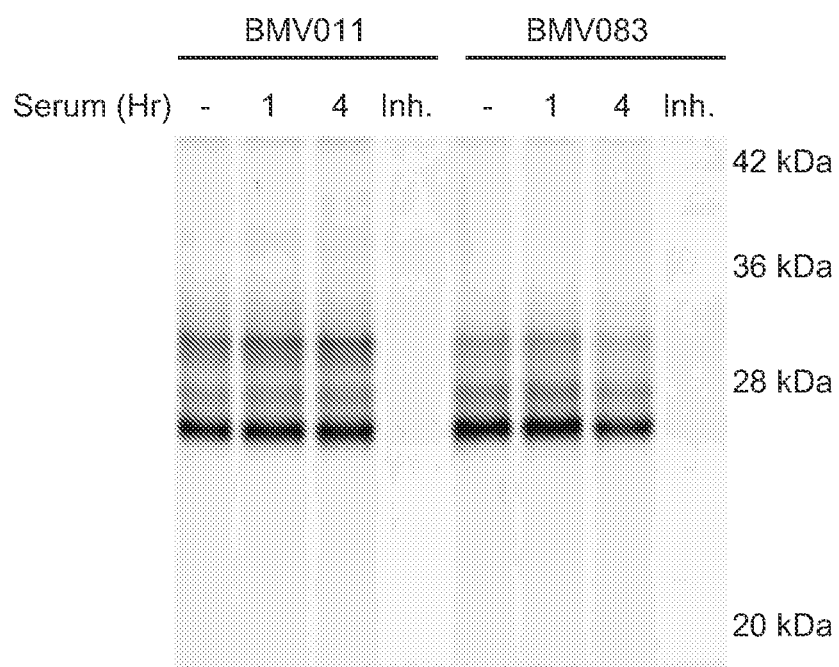

Referring now to FIG. 6, RAW cells were exposed to various concentrations of exemplary compounds BMV011 and BMV 083. As indicated in the legend to this figure, specific labeling of cathepsin B, S and L was shown in RAW cells, even after exposure of the test compounds to serum, indicating stability of the compounds is suitable for in vivo applications.

Example 4

Topical Application of Probes

Figure 7:
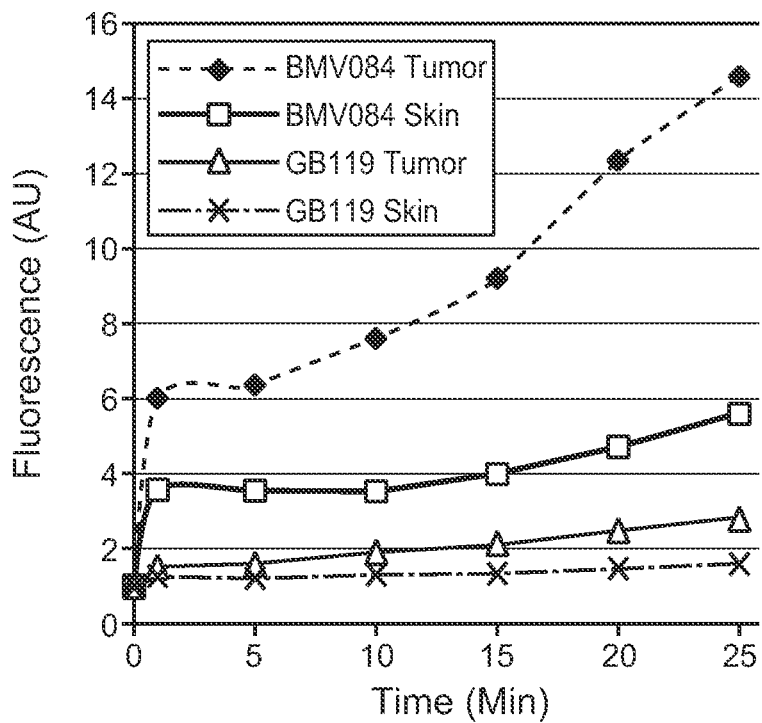
FIG. 7 is a line graph showing fluorescence over time after topical application of BMV084. Subcutaneously grown mouse breast cancer allografts were cut in half and a solution of 1 μM GB119 or BMV084 in DMSO was applied to the surface. As a control, skin surrounding the tumor was treated with an equal amount of probe. Increase in fluorescence was measured over time. BMV084 fluorescence activation was more than two times enhanced on tumor tissue compared to skin tissue. Fluorescence activation of BMV084 compared to GB119 was more than four times enhanced.

Referring now to FIG. 7, fluorescence over time was measured after topical application of various compounds. Tumor allografts showed specific labeling by BMV 084 which is superior to a prior art peptide-based probe (e.g. GB119).

Example 5

Non-Invasive Imaging of Tumors of Mice Injected with BMV011 and BMV083

Figure 8:
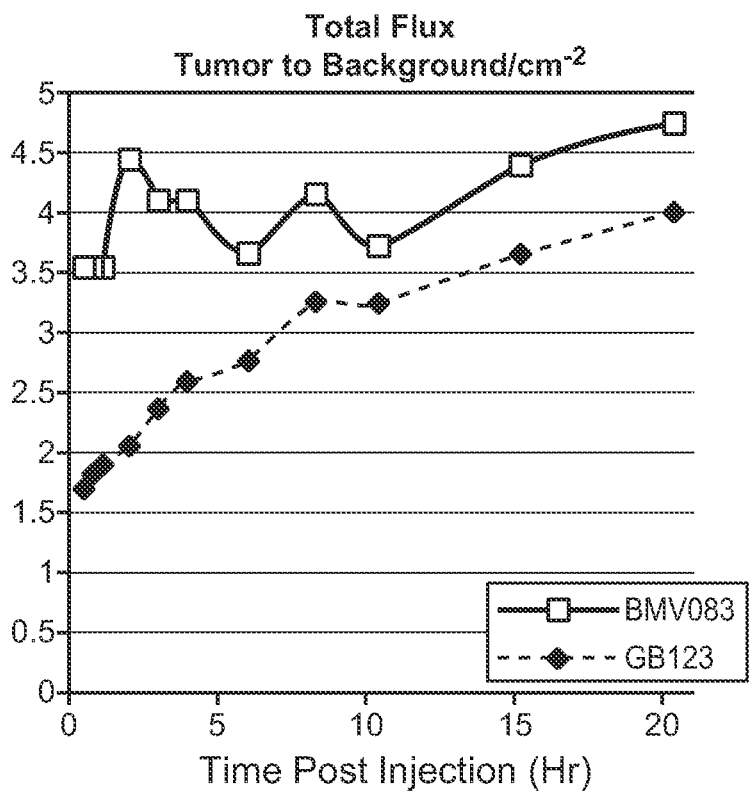
FIG. 8 is a graph showing a comparison of fluorescent tumor signal after systemic delivery of the non-quenched first generation fluorescent imaging probe GB123 (4) and the novel, non-peptidic quenched fluorescent imaging probe BMV083 (2). Mice bearing 4T1 allograft tumors were injected with 20 nmol GB123 or BMV083 and the mice were imaged for Cy5 fluorescence over time. At early time points, the tumor to background ratio is about two fold higher for the new generation quenched fluorescent imaging probe BMV083 compared to the non-quenched first generation probe GB123. Over time, the two probes approach similar tumor to background ratios.

FIG. 8 shows tumor to background ratio from non-invasive imaging with the IVIS system, exemplary compound BMV083 was administered to a mice bearing allograft tumors. The tumor to background ratio of the present BMV083 is superior to that of the prior art GB123 at early time points, thus making the new probes more valuable for fast imaging applications and for real time imaging applications that are not possible with previous generation probes.

Other protocols are known and may be adapted for administration and imaging in vivo using the present compounds. Another protocol for mouse studies is given in Joyce et al. "Cathepsin cysteine proteases are effectors of invasive growth and angiogenesis during multistage tumorigenesis," Cancer Cell 5:443-452 (May 2004), at page 452.

Figure 9:
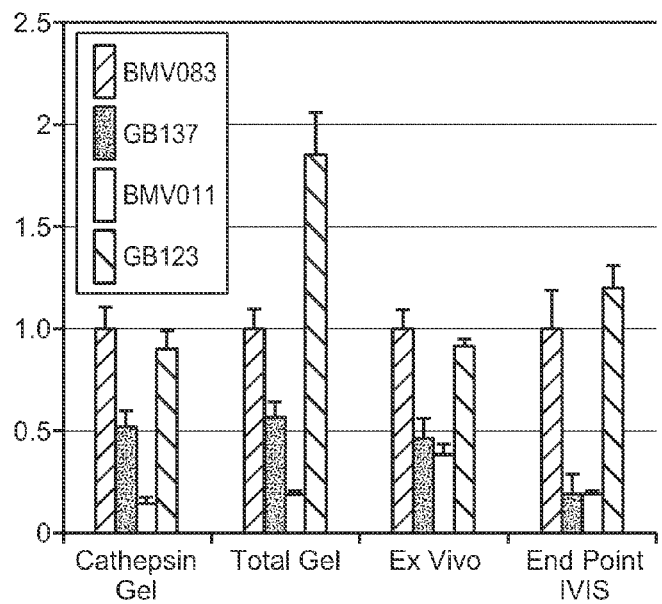
FIG. 9 is a bar graph showing four sets of bar graphs that illustrate a correlation between non-invasive imaging data and cathepsin labeling for both quenched (BMV083 and GB137 and non-quenched (GB123 and BMV011) probes under different conditions. Mice bearing 4T1 allografts were injected with 20 nmol non-peptidic quenched fluorescent imaging probe BMV083 (2), quenched fluorescent imaging probe GB137 (5), non-peptidic fluorescent imaging probe BMV011 (1) or fluorescent imaging probe GB123 (4). 20 hours post injection, the mice were imaged on the IVIS system and the tumor fluorescence was quantified (end point IVIS). The tumors were excised and imaged ex vivo (Ex Vivo). Tissue lysates were made and the proteins were resolved on 15% SDS-PAGE, after which the cathepsin labeling (Cathepsin Gel) and off target labeling (Total Gel) was quantified. The novel, non-peptidic quenched fluorescent imaging probe BMV083 (2) reflects cathepsin activity non-invasively with high sensitivity and selectivity. The original peptidic probes show some off target labeling and provide less bright signal compared to the non-peptidic probes.
Figure 10A:
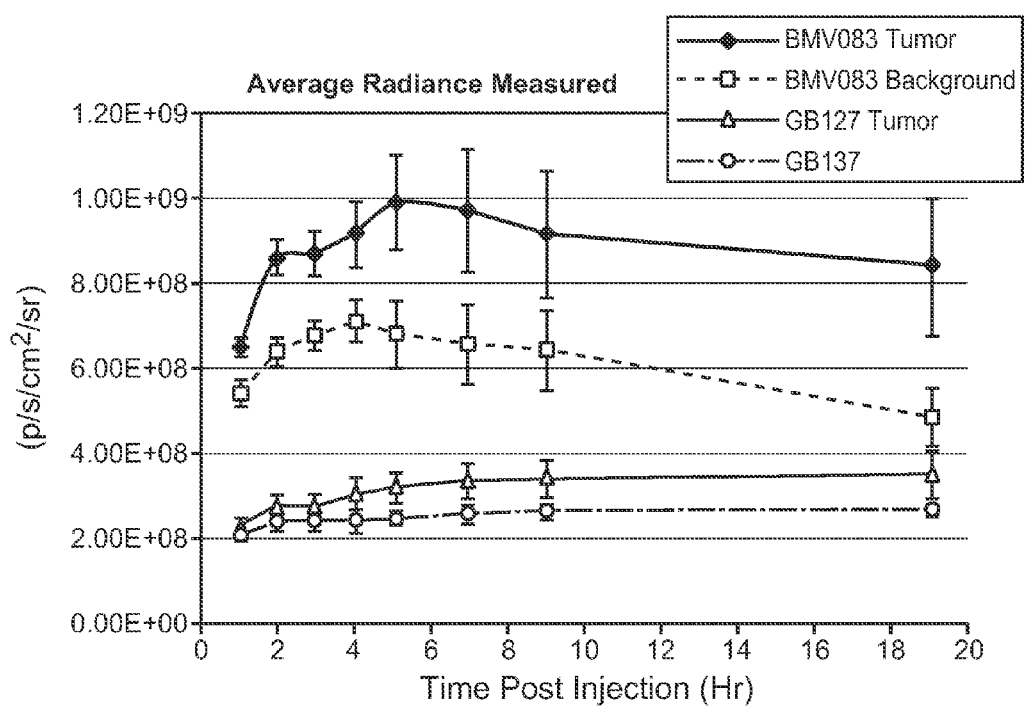
FIG. 10A and FIG. 10B is a pair of graphs (10A, 10B)
Figure 10B:
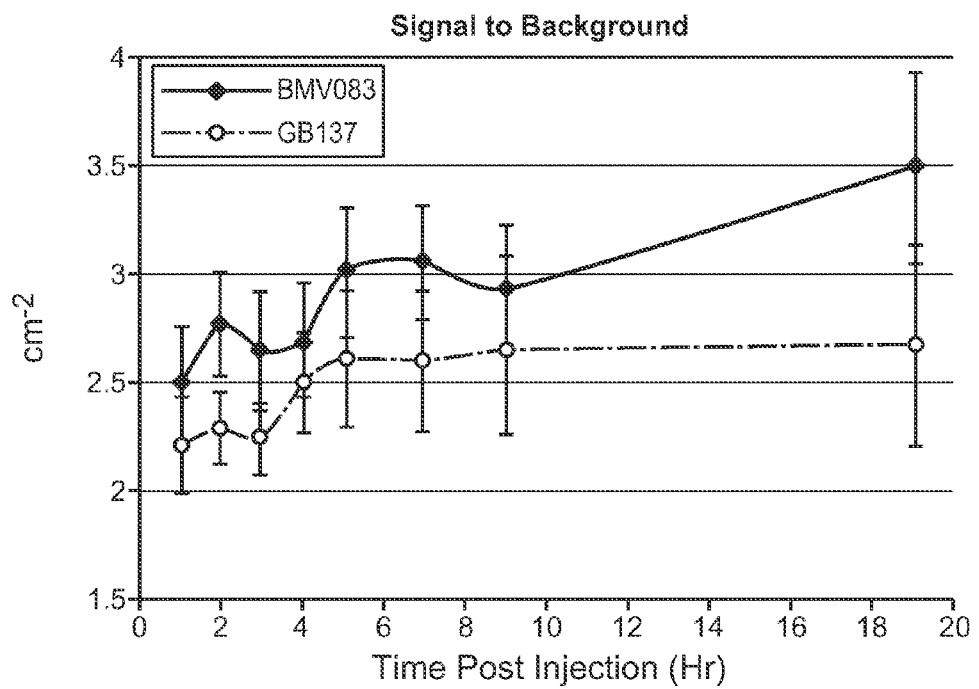
Figure 10C:
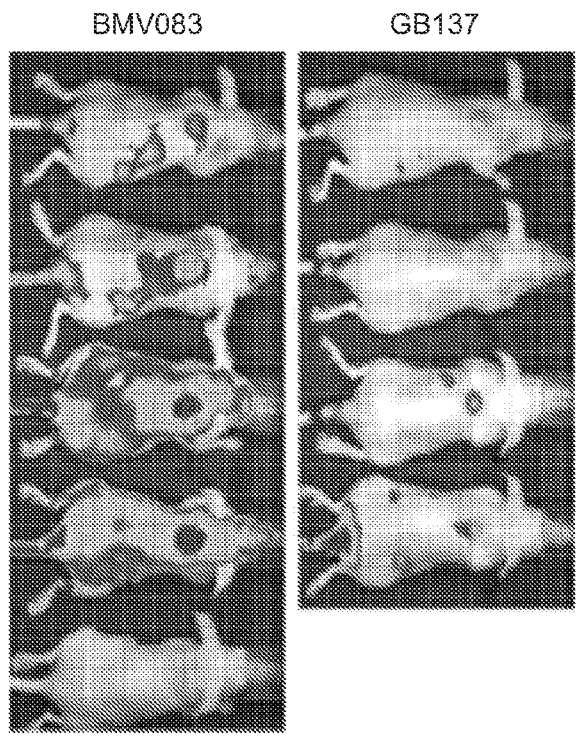
FIG. 10C is a photograph illustrating a comparison of non-invasive imaging of tumor cathepsin activity with the novel, non-peptidic quenched fluorescent imaging probe BMV083 (compound 2) and quenched fluorescent imaging probe GB137 (compound 5). Mice bearing 4T1 allografts were injected with 20 nmol non-peptidic quenched fluorescent imaging probe BMV083 (2) or quenched fluorescent imaging probe GB137 (5) and were imaged for Cy5 fluorescence over time.

As shown by the bar graph in FIG. 9, and the data in FIG. 10, the imaging data correlated with the cathepsin labeling data under a variety of circumstances. The present compounds showed a high signal to background and little off target labeling.

In summary, it was found that by combining the quenched probe with the new spectral imager technology, that it is possible to image cathepsin activity in live animals using an activity-based probe. A possible further improvement would be the modification of the quenched probe to include a fluorescent tag in the far-red region, which further diminishes background fluorescence and enhances tissue penetration of light.

Example 6

Labeling in Breast Cancer Model

BMV083 was tested in a more physiologically relevant orthotopic mouse breast cancer model. For this model, the 4T1 cell line isolated from a spontaneously arising BALB/c mammary tumor was implanted into the mammary fat pad of BALB/c mice with an intact immune system. This is especially important since host-tumor interactions and immune cell infiltration in the tumor microenvironment are important factors in tumor development. 4T1 cells expressing both GFP and luciferase (4T1-luc-GFP) were implanted in the number 2 and 7 mammary fat pad and tumor growth was monitored.

Tumor bearing mice were then intraperitoneally injected with luciferin 10 hours post probe injection followed by imaging for bioluminescence and probe derived Cy5 fluorescence. The 4T1-luc-GFP cancer cell derived luciferase bioluminescence demarcated the tumor boundaries and BMV083 activation was localized to the same area, indicating elevated cathepsin activity in the 4T1 tumor microenvironment. Interestingly, compared to the allograft model, fluorescence analysis of the SDS-PAGE resolved protein content revealed cathepsin S as the major in vivo target for BMV083 with only minor labeling of cathepsin B (cathepsin S represents 82.0±0.7% (n=6) of total labeling intensity). A biodistribution study was performed, showing that similar to GB137, the primary target organs of BMV083 are the liver and spleen. Ex vivo labeling of the active cathepsin content in whole organ homogenates with the BODIPY TMR labeled BMV099 indicated a high degree of cathepsin activity in the organs that are strongly labeled in vivo. Interestingly, although there are high levels of cathepsin activity in the kidney, it is not effectively targeted by BMV083 indicating specific partitioning of the probe to certain organs. On a similar note, the total cathepsin activity in the tumor was relatively low; however, the BMV083 signal in tumors is relatively high, again suggesting partitioning of the probe to specific tissues.

Example 7

Labeling of Macrophages

Tumor-associated macrophages play important roles in tumor development and have been shown to promote angiogenesis, tumor growth and invasiveness, and macrophage infiltration into tumors has been correlated with poor clinical outcome in several cancers. The activation state acquired by the infiltrating macrophage in the tumor microenvironment determines its effect on the tumor. Macrophages with the M2 phenotype exhibit tumor promoting characteristics, whereas M1 macrophages are able to eradicate tumors. The macrophage activation state is plastic and tumor promoting macrophages can be re-educated into tumor killing M1 macrophages, for example, by local treatment with Granulocyte Macrophage ColonyStimulating Factor. Non-invasive imaging tools that report on the tumor promoting M2 type tumor-associated macrophage content could be of prognostic value.

Therefore, the cellular source of BMV083 derived fluorescence in vivo was studied. Since macrophages have previously been shown to possess high cathepsin activity in the tumor and the fact that the amount of F4/80 expression is indicative of the macrophage activation state, four populations of cells from the 4T1-luc-GFP syngeneic orthotopic tumors were analyzed for BMV083 fluorescence. These included two populations of F4/80 expressing cells (F4/80DIM and F4/80HI) and from the F4/80-population, cells that did not express GFP (F4/80-GFP−) and a population containing the GFP expressing tumor cells (F4/80-GFP+). The F4/80HI population was responsible for the majority of BMV083 activation, with a more than twelvefold increase in Cy5 mean fluorescence compared to vehicle treatment (data not shown). To confirm this observation, the four cell populations were isolated in high purity using flow cytometric cell sorting, followed by gel analysis of fluorescently labeled cathepsins. Equal cell numbers per population were lysed and the active cathepsin content was labeled ex vivo with BMV099. This ex vivo labeling confirmed that in vivo probe labeling correlated with the absolute levels of cathepsins that were expressed and active in each cell population and was not the result of unequal uptake of the probe by the different cell populations. Consistent with the overall mean fluorescence levels, the F4/80HI population showed the most robust labeling of cathepsin S and to a lesser extent cathepsin B, similar to the labeling profile observed in whole tumor homogenates. Weaker labeling intensities were observed in the other three populations, with a slightly more pronounced labeling in the F4/80DIM population. A similar trend was also observed when analyzing the same gel for ex vivo BMV099 labeled cathepsins, showing the highest cathepsin activity in the F4/80HI population. Interestingly, the degree of F4/80 expression seems to correlate with cathepsin activity, which suggests that cathepsin activity could be indicative of differences in activation phenotypes of myeloid derived cells.

To further investigate which sub-populations of macrophages have the highest levels of cathepsin activity in the tumor microenvironment, three markers were used to identify the activation state of the labeled myeloid derived cells. CD11b+ Gr-1+ myeloid derived suppressorcells (MDSCs) have been shown to possess high cathepsin activity in the APCΔ468 mouse model of hereditary polyposis. It is also generally believed that tumor associated macrophages (TAMs) possess an M2 like macrophage character. The macrophage mannose receptor (MMR, also known as CD206), was therefore included, the expression of which is elevated in M2 compared to M1 macrophages.

Because of recent reports concerning the immunogenicity of GFP in Balb/c mice, we also implanted 4T1 cells lacking the GFP reporter were also implanted in the number 2 and 7 mammary fat pad of Balb/c mice. BMV083 was systemically administered via tail vein injection and excised tumors at 10 hours post injection to generate single cell suspensions. Consistent with the results in the 4T1-luc-GFP tumors, the highest degree of probe activation was observed in the F4/80HI cell population as determined by FACS analysis (CD11b+F4/80HI). To further characterize the probe positive cells, the CD11b+F4/80HI population was analyzed for Gr-1 and MMR expression. This analysis determined that BMV083 labeling occurs most predominantly in CD11b+F4/80HI cells that express MMR. Furthermore, of the CD11b+F4/80HIMMR+ cells, the Gr-1 expressing population showed more than 2 fold higher probe accumulation compared to the Gr-1 negative population. This data indicates that the CD11b+F4/80HIMMR+Gr-1+ cells are the major cellular source of cathepsin S activity in the 4T1 tumor microenvironment. CD11b+F4/80+Gr-1+ cells in mouse models of cancer have been defined as myeloid-derived suppressor cells (MDSCs). In response to TLR4 ligands released from damaged tumor cells, MDSCs inhibit antitumor T cell responses by inducing apoptosis in activated T cells.

The data presented here shows that the cathepsin S directed non-peptidic NIRF qABP BMV083 has improved in vivo properties compared to previously developed ABPs. In the syngeneic 4T1 mouse model for breast cancer, this probe primarily reports on the cathepsin activity in the tumor promoting M2 type CD11b+F4/80HIMMR+ macrophages. Of these, the Gr-1 expressing MDSCs constitute the highest degree of probe activation. Because infiltration of these cell types into the tumor microenvironment plays important roles in tumor development and the fact that their occurrence is correlated with poor prognosis and negative effects on tumor immunotherapy, BMV083 could be of prognostic value.

The present examples, methods, procedures, specific compounds and molecules are meant to exemplify and illustrate the invention and should in no way be seen as limiting the scope of the invention, which is defined by the literal and equivalent scope of the appended claims. Any patents or publications mentioned in this specification are indicative of levels of those skilled in the art to which the patent pertains and are intended to convey details of the invention which may not be explicitly set out but would be understood by workers in the field. Such patents or publications are hereby incorporated by reference to the same extent as if each was specifically and individually incorporated by reference and for the purpose of describing and enabling the method or material referred to.

REFERENCES

1. Baruch, A., Jeffery, D. A. & Bogyo, M. Enzyme activity—it's all about image. Trends Cell Biol 14, 29-35 (2004).
2. Berger, A. B., Vitorino, P. M. & Bogyo, M. Activity-based protein profiling: applications to biomarker discovery, in vivo imaging and drug discovery. Am J Pharmacogenomics 4, 371-81 (2004).
3. Speers, A. E. & Cravatt, B. F. Chemical strategies for activity-based proteomics. Chembiochem 5, 41-7 (2004).
4. Jeffery, D. A. & Bogyo, M. Chemical proteomics and its application to drug discovery. Curr Opin Biotechnol 14, 87-95 (2003).
5. Adam, G. C., Sorensen, E. J. & Cravatt, B. F. Chemical strategies for functional proteomics. Mol Cell Proteomics 1, 781-90 (2002).
6. Jessani, N. & Cravatt, B. F. The development and application of methods for activity-based protein profiling. Curr Opin Chem Biol 8, 54-9 (2004).
7. Liu, Y., Patricelli, M. P. & Cravatt, B. F. Activity-based protein profiling: the serine hydrolases. Proc Natl Acad Sci USA 96, 14694-9 (1999).
8. Saghatelian, A., Jessani, N., Joseph, A., Humphrey, M. & Cravatt, B. F. Activity-based probes for the proteomic profiling of metalloproteases. Proc Natl Acad Sci USA 101, 10000-5 (2004).
9. Greenbaum, D. et al. Chemical approaches for functionally probing the proteome. Mol Cell Proteomics 1, 60-8 (2002).
10. Joyce, J. A. et al. Cathepsin cysteine proteases are effectors of invasive growth and angiogenesis during multistage tumorigenesis. Cancer Cell 5, 443-53 (2004).
11. Okerberg, E. S. et al. High-resolution functional proteomics by active-site peptide profiling. Proc Natl Acad Sci USA 102, 4996-5001 (2005).
12. Bieth, J. G. Theoretical and practical aspects of proteinase inhibition kinetics. Methods Enzymol 248, 59-84 (1995).

What is claimed is:

1. A compound according to Formula I

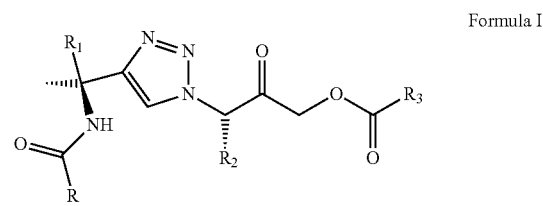

Formula I where

R is either a 4-7 member aromatic ring or a 4-7 member cycloalkyl group, said aromatic ring or said cycloalkyl group having therein 0 to 5 heteroatoms which are one or more of N, O, S, Si, B or Ar;

R1 is lower alkyl;

R2 is selected from the group consisting of lower alkyl, alkoxy, alkyl amine and alkyl amide; and R3 is selected from the group consisting of aryl, lower alkyl, alkoxy, alkyl amine and alkyl amide; provided that at least one of R, R1, R2, and R3 is linked to a fluorophore; and R, R1, R2 and R3 are optionally linked to a quencher for said fluorphore, and said fluorophore and said quencher are present either as (i) only a fluorophore or (ii) a fluorophore and a quencher pair where one member of the pair is on R, R1, or R2 and another member of the pair is on R3.

2. The compound of claim 1 wherein R is selected from the group consisting of

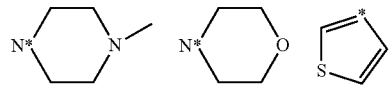

where * indicates a point of attachment of the bond shown in Formula I.

3. The compound of claim 1 wherein R3 is dimethyl phenyl.

4. The compound of claim 1 wherein R3 is dimethyl phenyl linked to a quencher.

5. The compound of claim 1 comprising a Flu/Qu pair that is a bora-diaza-indecene and a diaryl rhodamine.

6. The compound of claim 1 comprising a Flu/Qu pair that is cyanine and QSY.

7. The compound of claim 1 comprising a Flu/Qu pair that is Cy5 and QSY21.

8. A composition useful for imaging one or more cells associated with cathepsin activity, comprising a compound according to claim 1, in purified form.

9. The composition of claim 8, further comprising excipients and suitable for in vivo administration.

10. The composition of claim 8 wherein R is selected from the group consisting of

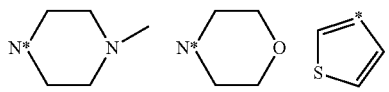

where * indicates a point of attachment of the bond shown in Formula I.

11. The composition of claim 8 wherein R3 is dimethyl phenyl.

12. The composition of claim 8 wherein R3 is dimethyl phenyl linked to a quencher.

13. A composition according to claim 8 wherein said compound is according to Formula II below Formula II

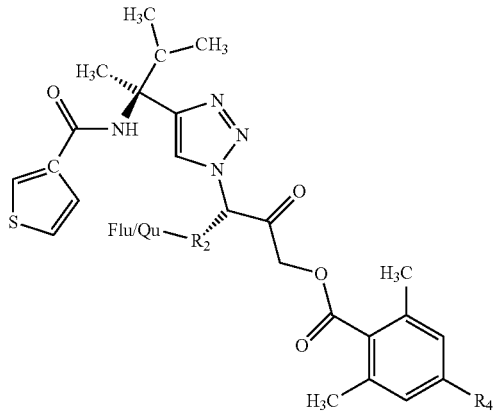

wherein R2 is a linker to Flu/Qu, where Flu/Qu is either a fluorphore or a quencher, said linker selected from the group consisting of lower alkyl, lower alkoxy, lower alkyl amine and lower alkyl amide; or R2 is a capping group if Flu/Qu is absent; and R4 is H or Flu/Qu.

14. The compound of claim 13 comprising a Flu/Qu pair that is a bora-diaza-indecene and a diaryl rhodamine.

15. The compound of claim 13 comprising a Flu/Qu pair that is cyanine and QSY.

16. The compound of claim 13 comprising a Flu/Qu pair that is Cy5 and QSY21.

17. A composition according to claim 8 wherein said compound is according to Formula III below Formula III

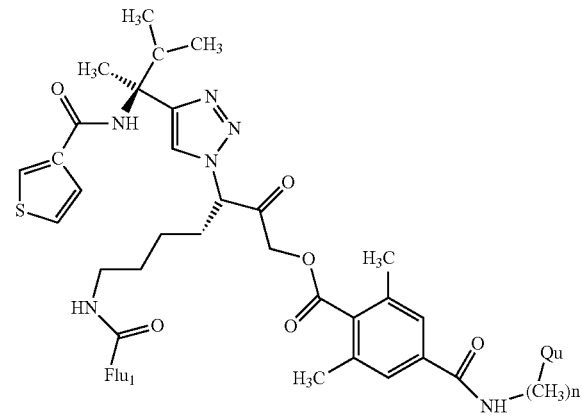

wherein n is between 1 and 5 and Flu1 and Qu are a fluorophore-quencher pair.

18. The compound of claim 17 comprising a Flu1/Qu pair that is a bora-diaza-indecene and a diaryl rhodamine.

19. The compound of claim 17 comprising a Flu1/Qu pair that is cyanine and QSY.

20. The compound of claim 17 comprising a Flu1/Qu pair that is Cy5 and QSY21.

21. The compound of claim 1 comprising a Flu/Qu pair that is a bora-diaza-indecene and a diaryl rhodamine.

22. The compound of claim 1 comprising a Flu/Qu pair that is cyanine and QSY.

23. The compound of claim 1 comprising a Flu/Qu pair that is Cy5 and QSY21.

24. A compound according to Formula II below

Formula II

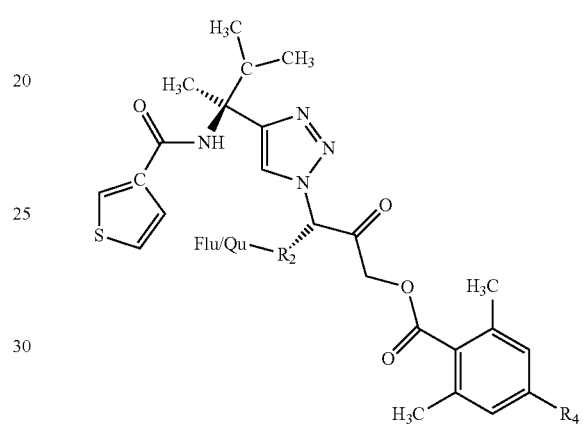

wherein R2 is a linker to Flu/Qu, where Flu/Qu is either a fluorphore or a quencher, said linker selected from the group consisting of lower alkyl, lower alkoxy, lower alkyl amine and lower alkyl amide; or R2 is a capping group if Flu/Qu is absent; and R4 is H or Flu/Qu.

25. The compound of claim 24 comprising a Flu/Qu pair that is a bora-diaza-indecene and a diaryl rhodamine.

26. The compound of claim 24 comprising a Flu/Qu pair that is cyanine and QSY.

27. The compound of claim 24 comprising a Flu/Qu pair that is Cy5 and QSY21.

28. A compound according to Formula III below

Formula III

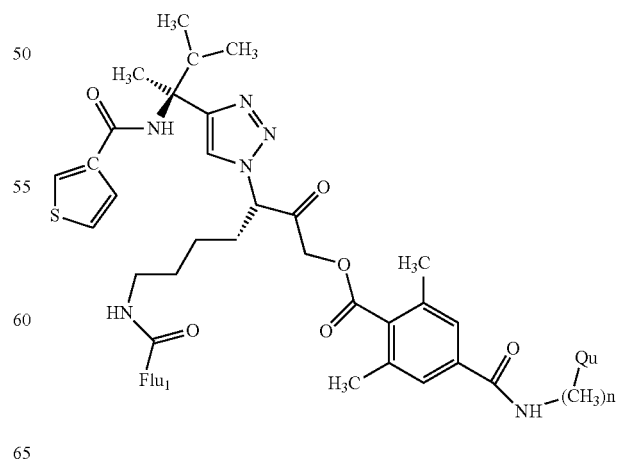

wherein n is between 1 and 5 and $Flu_1$ and Qu are a fluorophore-quencher pair.

29. The compound of claim 28 comprising a $Flu_1/Qu$ pair that is a bora-diaza-indecene and a diaryl rhodamine.

30. The compound of claim 28 comprising a $Flu_1/Qu$ pair that is cyanine and QSY.

31. The compound of claim 28 comprising a $Flu_1/Qu$ pair that is Cy5 and QSY21.

\* \* \* \* \*